US007531497B2

(12) United States Patent
Midha et al.

(10) Patent No.: US 7,531,497 B2
(45) Date of Patent: May 12, 2009

(54) PERSONAL CARE COMPOSITION CONTAINING A CLEANSING PHASE AND A BENEFIT PHASE

(75) Inventors: Sanjeev Midha, Mason, OH (US); Robert Lee Wells, Cincinnati, OH (US); Bryan Gabriel Comstock, Mason, OH (US); James Merle Heinrich, Fairfield, OH (US); Michael Frederick Niebauer, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 58 days.

(21) Appl. No.: 11/227,379

(22) Filed: Sep. 15, 2005

(65) Prior Publication Data

US 2006/0079422 A1 Apr. 13, 2006

Related U.S. Application Data

(60) Provisional application No. 60/617,392, filed on Oct. 8, 2004.

(51) Int. Cl.
*A61K 8/03* (2006.01)
*C11D 1/12* (2006.01)
*C11D 3/37* (2006.01)
*C11D 9/22* (2006.01)
*C11D 17/00* (2006.01)

(52) U.S. Cl. .................. 510/417; 510/119; 510/121; 510/122; 510/147; 510/159; 510/406; 510/419; 424/401; 424/70.1; 424/70.11; 424/70.12; 424/70.19

(58) Field of Classification Search .......... 510/119, 510/121, 122, 147, 159, 406, 417, 419; 424/401, 424/70.1, 70.11, 70.12, 70.19
See application file for complete search history.

(56) References Cited

U.S. PATENT DOCUMENTS

| | | |
|---|---|---|
| 2,438,091 A | 3/1948 | Lynch |
| 2,528,378 A | 10/1950 | Mannheimer |
| 2,658,072 A | 11/1953 | Kosmin |
| 2,694,668 A | 11/1954 | Fricke |
| 2,809,971 A | 10/1957 | Bernstein et al. |
| 2,826,551 A | 3/1958 | Geen |
| 3,152,046 A | 10/1964 | Kapral |
| 3,236,733 A | 2/1966 | Karsten et al. |
| 3,479,429 A | 11/1969 | Morshauser et al. |
| 3,533,955 A | 10/1970 | Pader et al. |
| 3,615,972 A | 10/1971 | Morehouse et al. |
| 3,753,196 A | 8/1973 | Kurtz et al. |
| 3,761,418 A | 9/1973 | Parran |
| 3,929,678 A | 12/1975 | Laughlin et al. |
| 3,937,811 A | 2/1976 | Papantoniou et al. |
| 3,958,581 A | 5/1976 | Abegg et al. |
| 3,962,418 A | 6/1976 | Birkofer |
| 3,964,500 A | 6/1976 | Drakoff |
| 4,089,945 A | 5/1978 | Brinkman et al. |
| 4,152,416 A | 5/1979 | Spitzer et al. |
| 4,159,028 A | 6/1979 | Barker et al. |
| 4,197,865 A | 4/1980 | Jacquet et al. |
| 4,217,914 A | 8/1980 | Jacquet et al. |
| 4,263,363 A | 4/1981 | Buck et al. |
| 4,323,683 A | 4/1982 | Bolich, Jr. et al. |
| 4,335,103 A | 6/1982 | Baker et al. |
| 4,345,080 A | 8/1982 | Bolich, Jr. |
| 4,364,837 A | 12/1982 | Pader |
| 4,379,753 A | 4/1983 | Bolich, Jr. |
| 4,381,919 A | 5/1983 | Jacquet et al. |
| 4,422,853 A | 12/1983 | Jacquet et al. |
| 4,425,322 A | 1/1984 | Harvey et al. |
| 4,470,982 A | 9/1984 | Winkler |
| 4,507,280 A | 3/1985 | Pohl et al. |
| 4,518,578 A | 5/1985 | Hayes et al. |
| 4,529,586 A | 7/1985 | DeMarco et al. |
| 4,663,158 A | 5/1987 | Wolfram et al. |
| 4,885,107 A | 12/1989 | Wetzel |
| 4,964,874 A | 10/1990 | Saphakkul |
| 4,970,252 A | 11/1990 | Sakuta et al. |
| 4,980,155 A | 12/1990 | Shah et al. |
| 5,059,414 A * | 10/1991 | Dallal et al. ............... 424/70.2 |
| 5,061,481 A | 10/1991 | Suzuki et al. |

(Continued)

FOREIGN PATENT DOCUMENTS

CA 2246316 6/1998

(Continued)

OTHER PUBLICATIONS

XP 002332778 "Dove All Day Moisturizing Body Wash" Online URL: http://www.ewg.org/reports/skindeep2/report.php?type=PRODUCT&id=8801874, Apr. 2005.

(Continued)

*Primary Examiner*—Brian P Mruk
(74) *Attorney, Agent, or Firm*—Laura R. Grunzinger; Angela K. Haughey; Andrew J. Hagerty

(57) ABSTRACT

Personal care compositions comprising a cleansing phase and a benefit phase. These products are intended to provide a multi-phase personal care composition that is packaged in physical contact while remaining stable and providing improved in-use and after-use hair and skin benefits.

18 Claims, No Drawings

U.S. PATENT DOCUMENTS

| | | |
|---|---|---|
| 5,100,657 A | 3/1992 | Ansher-Jackson et al. |
| 5,100,658 A | 3/1992 | Bolich, Jr. et al. |
| 5,104,646 A | 4/1992 | Bolich, Jr. et al. |
| 5,106,609 A | 4/1992 | Bolich, Jr. et al. |
| 5,228,189 A | 7/1993 | Driller et al. |
| 5,281,240 A | 1/1994 | McGee |
| RE34,584 E | 4/1994 | Grote et al. |
| 5,393,450 A | 2/1995 | Shana'a et al. |
| 5,412,004 A | 5/1995 | Tachibana et al. |
| 5,455,035 A | 10/1995 | Guerrero et al. |
| 5,487,168 A | 1/1996 | Geiner et al. |
| 5,556,628 A | 9/1996 | Derian et al. |
| 5,612,307 A | 3/1997 | Chambers et al. |
| 5,635,171 A | 6/1997 | Nadaud et al. |
| 5,654,362 A | 8/1997 | Schulz, Jr. et al. |
| 5,661,189 A | 8/1997 | Grievson et al. |
| 5,674,478 A | 10/1997 | Dodd et al. |
| 5,750,122 A | 5/1998 | Evans et al. |
| 5,760,116 A | 6/1998 | Kilgour et al. |
| 5,811,487 A | 9/1998 | Schulz, Jr. et al. |
| 5,837,793 A | 11/1998 | Harashima et al. |
| 5,851,978 A | 12/1998 | Shana'a |
| 5,929,019 A | 7/1999 | Puvvada et al. |
| 5,947,335 A | 9/1999 | Milio et al. |
| 5,952,286 A | 9/1999 | Puvvada et al. |
| 5,965,500 A | 10/1999 | Puvvada |
| 6,174,845 B1 | 1/2001 | Rattinger et al. |
| 6,176,391 B1 | 1/2001 | Rehkemper et al. |
| 6,176,395 B1 | 1/2001 | Abbott et al. |
| 6,190,648 B1 | 2/2001 | Kouzu et al. |
| 6,213,166 B1 | 4/2001 | Thibiant et al. |
| 6,245,323 B1 | 6/2001 | Christie et al. |
| 6,245,344 B1 | 6/2001 | Thibiant et al. |
| 6,268,322 B1 | 7/2001 | St. Lewis et al. |
| 6,306,806 B1 | 10/2001 | St. Lewis et al. |
| 6,340,723 B1 | 1/2002 | Nita et al. |
| 6,383,999 B1 | 5/2002 | Coyle et al. |
| 6,429,177 B1 | 8/2002 | Salmon et al. |
| 6,506,391 B1 | 1/2003 | Biatry |
| 6,517,939 B1 | 2/2003 | Ramin et al. |
| 6,534,456 B2 | 3/2003 | Hayward et al. |
| 6,534,457 B2 | 3/2003 | Mitra |
| 6,673,755 B2 | 1/2004 | Wei et al. |
| 2001/0036467 A1 | 11/2001 | Thibiant et al. |
| 2002/0004468 A1 | 1/2002 | Hodge et al. |
| 2002/0010110 A1* | 1/2002 | Hayward et al. ............ 510/130 |
| 2003/0152540 A1 | 8/2003 | Putman et al. |
| 2003/0161852 A1 | 8/2003 | Miller et al. |
| 2003/0180246 A1 | 9/2003 | Frantz et al. |
| 2003/0222100 A1 | 12/2003 | Husband et al. |
| 2004/0048757 A1 | 3/2004 | Zhang et al. |
| 2004/0048758 A1 | 3/2004 | Zhang et al. |
| 2004/0057920 A1 | 3/2004 | Focht et al. |
| 2004/0092415 A1 | 5/2004 | Focht et al. |
| 2004/0105827 A1 | 6/2004 | Grimm et al. |
| 2004/0158940 A1 | 8/2004 | Wells et al. |
| 2004/0219119 A1 | 11/2004 | Wei et al. |
| 2004/0223929 A1 | 11/2004 | Clapp et al. |
| 2004/0223939 A1 | 11/2004 | Clapp et al. |
| 2004/0223991 A1 | 11/2004 | Wei et al. |
| 2004/0235693 A1* | 11/2004 | Wei et al. .................... 510/130 |
| 2004/0242706 A1 | 12/2004 | Wiersema et al. |
| 2004/0248748 A1 | 12/2004 | Wei et al. |
| 2005/0020468 A1 | 1/2005 | Frantz et al. |
| 2005/0100570 A1 | 5/2005 | Wei et al. |
| 2005/0143269 A1 | 6/2005 | Wei et al. |
| 2005/0192187 A1 | 9/2005 | Wagner et al. |
| 2005/0192188 A1 | 9/2005 | Wagner et al. |
| 2005/0192189 A1 | 9/2005 | Wagner et al. |
| 2005/0238680 A1 | 10/2005 | Stella et al. |
| 2005/0276768 A1 | 12/2005 | Wei et al. |
| 2006/0002880 A1 | 1/2006 | Peffly et al. |

FOREIGN PATENT DOCUMENTS

| | | |
|---|---|---|
| DE | 196 50 952 A | 6/1998 |
| DE | 198 54 086 A | 5/2000 |
| EP | 0056219 A1 | 7/1982 |
| EP | 0 078138 A2 | 5/1983 |
| EP | 078138 * | 5/1983 |
| EP | 0112807 A2 | 7/1984 |
| EP | 0320473 A1 | 6/1989 |
| EP | 0348372 A2 | 12/1989 |
| EP | 0408311 A2 | 1/1991 |
| EP | 0 331617 B | 4/1992 |
| EP | 0486080 A2 | 5/1992 |
| EP | 1 108421 A2 | 6/2001 |
| EP | 1 005849 B1 | 9/2001 |
| EP | 1 064918 B1 | 9/2002 |
| EP | 0 907345 B1 | 5/2003 |
| FR | 2673179 A1 | 8/1992 |
| GB | 849433 | 9/1960 |
| GB | 1277324 A | 6/1972 |
| JP | 61-18708 | 1/1986 |
| JP | 2000229817 A | 8/2000 |
| JP | 2002-128639 A | 5/2002 |
| JP | 2002-138010 A | 5/2002 |
| WO | WO 90/13283 A1 | 11/1990 |
| WO | WO 94/10973 A1 | 5/1994 |
| WO | WO 97/17938 A1 | 5/1997 |
| WO | WO 98/27193 A1 | 6/1998 |
| WO | WO 99/38489 A1 | 8/1999 |
| WO | WO 99/38491 A1 | 8/1999 |
| WO | WO 00/75240 A1 | 12/2000 |
| WO | WO 01/01931 A1 | 1/2001 |
| WO | WO 01/70193 A2 | 9/2001 |
| WO | WO 01/70926 A1 | 9/2001 |
| WO | WO 02/100358 * | 12/2002 |
| WO | WO 02/100358 A1 | 12/2002 |
| WO | WO 03/055456 A1 | 7/2003 |
| WO | WO 03/105796 A1 | 12/2003 |
| WO | WO 2004/018609 A1 | 3/2004 |
| WO | WO 2004/026276 A1 | 4/2004 |
| WO | WO 2004/050055 A1 | 6/2004 |
| WO | WO 2005/048959 A1 | 6/2005 |
| WO | WO 2005/067875 A1 | 7/2005 |
| WO | WO 2005/084614 A1 | 9/2005 |
| WO | WO 2005/084616 A1 | 9/2005 |

OTHER PUBLICATIONS

XP002332779 "Olay Daily Renewal Moisturizing Body Wash" Online URL: http://householdprdoucts.nlm.nih.gov/cgi-bin/household.brands?tbl=brands&id=16003084, Feb. 8, 2006.

PCT International Search Report dated Mar. 6, 2006, 12 pages.

U.S. Appl. No. 07/758,319, filed Aug. 27, 1991, Bolich, Jr. et al.

U.S. Appl. No. 07/758,320, filed Aug. 27, 1991, Torgerson et al.

* cited by examiner

PERSONAL CARE COMPOSITION CONTAINING A CLEANSING PHASE AND A BENEFIT PHASE

CROSS-REFERENCE TO RELATED APPLICATIONS

This application claims the benefit of U.S. Provisional Application No. 60/617,392 filed on Oct. 8, 2004, the disclosure of which is incorporated herein in its entirety by reference.

FIELD

The present invention relates to personal care compositions comprising a cleansing phase and an aqueous benefit phase. These products are intended to provide a multi-phase personal care composition that is packaged in physical contact while remaining stable and providing improved in-use and after-use hair and skin benefits.

BACKGROUND

Personal care compositions containing detersive surfactants and cationic polymers to improve deposition of conditioning oils capable of imparting conditioning or smoothness properties to surfaces treated therewith are known in the art. In addition to compositions that provide conditioning benefits, there are also compositions known in the art that provide other benefits such as coloring, styling, and a variety of hair health benefits. However, the level of additional benefits these compositions provide fall short of consumer expectations. In addition, when a benefit agent is included in a cleansing product, the amount of lather generated is reduced.

One attempt at providing multiple benefits (conditioning, coloring, styling, hair health) from a personal care product, while maintaining cleansing and high lather, has been the dual-chamber packaging. These packages comprise separate cleansing compositions and benefit compositions and allow for co-dispensing of the two in a single or dual stream. The separate benefit and cleansing compositions remain physically separate and stable during prolonged storage and just prior to application, then mix during or after dispensing to provide conditioning and cleansing benefits from a physically stable system. Although such dual-chamber delivery systems provide improved consumer benefits over the use of conventional systems, it is often difficult to achieve consistent and uniform performance because of the uneven dispensing ratio between the cleansing phase and the benefit phase from these dual chamber packages. Additionally, these packaging systems add considerable cost to the finished product.

Accordingly, the need still remains for personal care compositions that provide multiple benefits delivered from good cleansing products. The need also remains for personal care compositions comprising two or more phases in physical contact that remain stable.

SUMMARY

It is an object of the present invention to provide a multi-phase personal care composition comprising at least one cleansing phase and at least one aqueous benefit phase that are visually distinct phases that are packaged in physical contact and maintain stability, and the compositions provide improved in-use and after-use hair benefits.

The present invention is directed to a multi-phase personal care composition comprising at least one cleansing phase comprising at least one surfactant and at least one thickener; and at least one aqueous benefit phase comprising at least one thickener and at least one benefit agent selected from the group consisting of styling polymers, silicones, crosslinked silicone elastomers, peralkylene hydrocarbons, and hair coloring agents/dyes; wherein said cleansing phase and said benefit are visually distinct phases that are packaged in physical contact and maintain stability.

Benefit agents are useful in providing benefits including, but not limited to, enhanced perfume delivery, conditioning, foam, styling, hair volumizing, hair shine, hair coloring, hair moisturizing, hair health enhancing benefits.

DETAILED DESCRIPTION

The multi-phase personal cleansing compositions of the present invention comprise a first phase comprising a lathering cleansing phase, and at least one separate additional phase comprising a non-lathering structured aqueous phase. The non-lathering structured aqueous phase can be hydrophilic and in a preferred embodiment the non-lathering structured aqueous phase can be a hydrophilic gelled water phase. These and other essential limitations of the compositions and methods of the present invention, as well as many of the optional ingredients suitable for use herein, are described in detail hereinafter.

The essential components of the personal care composition are described below. Also included is a nonexclusive description of various optional and preferred components useful in embodiments of the present invention. While the specification concludes with claims that particularly point out and distinctly claim the invention, it is believed the present invention will be better understood from the following description.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt. %" herein.

All molecular weights as used herein are weight average molecular weights expressed as grams/mole, unless otherwise specified.

By the term "visually distinct," as used herein, is meant that the regions occupied by each phase can be separately seen by the human eye as distinctly separate regions in contact with one another (i.e. they are not emulsions or dispersions of particles of less than about 100 microns).

By the term "visibly clear" as used herein, is meant that the transmission of the composition is greater than 60%, preferably greater than 80%. The transparency of the composition is measured using Ultra-Violet/Visible (UV/VIS) Spectrophotometry, which determines the absorption or transmission of UV/VIS light by a sample. A light wavelength of 600 nm has been shown to be adequate for characterizing the degree of clarity of cosmetic compositions. Typically, it is best to follow the specific instructions relating the specific spectrophotometer being used. In general, the procedure for measuring percent transmittance starts by setting the spectrophotometer to the 600 nm. Then a calibration "blank" is run to calibrate the readout to 100 percent transmittance. The test sample is then placed in a cuvette designed to fit the specific spectrophotometer and the percent transmittance is measured by the spectrophotometer at 600 nm.

By the term "multi-phased" or "multi-phase" as used herein, is meant that at least two phases occupy separate and distinct physical spaces inside the package in which they are stored, but are in direct contact with one another (i.e., they are not separated by a barrier and they are not emulsified). In one preferred embodiment of the present invention, the "multi-phased" personal care compositions comprising at least two phases are present within the container as a visually distinct pattern. The pattern results from the mixing or homogenization of the "multi-phased" composition. The patterns include but are not limited to the following examples: striped, marbled, rectilinear, interrupted striped, check, mottled, veined, clustered, speckled, geometric, spotted, ribbons, helical, swirl, arrayed, variegated, textured, grooved, ridged, waved, sinusoidal, spiral, twisted, curved, cycle, streaks, striated, contoured, anisotropic, laced, weave or woven, basket weave, spotted, and tessellated. Preferably the pattern is selected from the group consisting of striped, geometric, marbled, and combinations thereof. In a preferred embodiment the striped pattern may be relatively uniform and even across the dimension of the package. Alternatively, the striped pattern may be uneven, i.e. wavy, or may be non-uniform in dimension. The striped pattern does not need to necessarily extend across the entire dimension of the package. The phases may be various different colors, or include particles, glitter or pearlescence.

The term "charge density", as used herein, refers to the ratio of the number of positive charges on a monomeric unit of which a polymer is comprised to the molecular weight of said monomeric unit. The charge density multiplied by the polymer molecular weight determines the number of positively charged sites on a given polymer chain.

The term "water soluble" as used herein, means that the component is soluble in water in the present composition. In general, the component should be soluble at about 25° C. at a concentration of about 0.1% by weight of the water solvent, preferably at about 1%, more preferably at about 5%, even more preferably at about 15%.

The term "anhydrous" as used herein, unless otherwise specified, refers to those compositions or materials containing less than about 10%, more preferably less than about 5%, even more preferably less than about 3%, even more preferably zero percent, by weight of water.

The term "ambient conditions" as used herein, unless otherwise specified, refers to surrounding conditions at one (1) atmosphere of pressure, 50% relative humidity, and 25° C.

The term "stable" as used herein, unless otherwise specified, refers to compositions in which the visible pattern or arrangement of the phases in different locations in the package is not significantly changing overtime when sitting in physical contact at ambient conditions for a period of at least about 180 days. In addition, it is meant that no separation, creaming, or sedimentation occurs. By "separation" is meant that the well-distributed nature of the visually distinct phases is compromised, such that larger regions of at least one phase collect until the balanced dispensed ratio of the two or more compositions relative to each other is compromised.

The term "personal care composition" as used herein, unless otherwise specified, refers to the compositions of the present invention, wherein the compositions are intended to include only those compositions for topical application to the hair or skin, and specifically excludes those compositions that are directed primarily to other applications such as hard surface cleansing, fabric or laundry cleansing, and similar other applications not intended primarily for topical application to the hair or skin.

The personal care compositions and methods of the present invention can comprise, consist of, or consist essentially of, the essential elements and limitations of the invention described herein, as well as any additional or optional ingredients, components, or limitations described herein or otherwise useful in personal care compositions intended for topical application to the hair or skin.

The present invention relates to personal care compositions comprising a cleansing phase and a benefit phase. These products are intended to provide a multi-phase personal care composition that is packaged in physical contact while remaining stable and providing improved in-use and after-use hair and skin benefits. In the present invention, the cleansing phase, the benefit phase, or both the cleansing phase and the benefit phase may be visibly clear. Alternatively, one of the phases is visibly clear and the other phase is opaque.

The compositions of the present invention preferably have a pH of from about 2 to about 8.5, more preferably from about 3 to about 7.5, even preferably from about 3.5 to about 6.5. Preferably, the ratio of the cleansing phase to the benefit phase is from about 10:1 to about 1:10. Other ratios of the cleaning phase to the benefit phase are contemplated by the present invention.

The cleansing phase exhibits a high viscosity, but it is highly shear thinning. The viscosities of the cleansing phase and the benefit phase are in the range of from about 10,000 centipoise to about 200,000,000 centipoise at stress measurements from about 1 to about 20 pascals, more preferably from about 100,000 to about 100,000,000 centipoise at stress measurements from about 1 to about 20 pascals. A Haake RS 150 RheoStress Rheometer may be used to determine the viscosity of the phases. The measurements are made under controlled stress conditions from about 1 pascal to about 500 pascals. A 60 mm parallel plate geometry with a plate gap size of about 0.75 mm is used for measurements. All measurements are taken at about 25° C.

Under appropriate composition, the cleansing phase can form lamellar or vesicle structures. Both lamellar and vesicle structures are considered liquid crystalline and are birefringent. Birefringent materials appear bright between cross-polarizers under an optical microscope.

A. Cleansing Phase

The personal care compositions of the present invention comprise a cleansing phase that comprises at least one surfactant and at least one thickener. The cleansing phase may additionally comprise any component listed in the benefit phase section herein or any component listed in the optional ingredient section herein. Preferably, the cleansing phase is present in an amount of from about 5% to about 95%, preferably from about 10% to about 90%, and more preferably from about 20% to about 80% by weight of the composition.

1. Surfactants

The cleansing phase of the present invention comprises at least one surfactant. Suitable surfactants for use herein include any known or otherwise effective cleansing surfactant which is suitable for application to the hair or skin, and which are otherwise compatible with the other essential ingredients in the cleansing phase of the compositions. The cleansing phase of the composition comprises at least one cleansing phase comprising at least one surfactant selected from the group consisting of anionic surfactants, nonionic surfactants, zwitterionic surfactants, amphoteric surfactants, cationic surfactants, soap, and mixtures thereof. Suitable surfactants are described in *McCutcheon's, Emulsifiers and Detergents* 1989 *Annual*, published by M. C. Publishing Co., and in U.S. Pat. No. 3,929,678.

The cleansing phase of the personal care compositions typically comprises a cleansing surfactant at concentrations ranging from about 4% to about 50%, more preferably from about 9% to about 30%. The surfactant may be present in an amount of at least 4% by weight of the composition of the cleansing phase, preferably at least about 9%. The preferred pH range of the cleansing phase is from about 5 to about 8, more preferably about 6.

Anionic surfactants suitable for use as cleansing surfactant in the cleansing phase of the present compositions include alkyl and alkyl ether sulfates. These materials have the respective formula $ROSO_3M$ and $RO(C_2H_4O)_xSO_3M$, wherein R is an alkyl or alkenyl of from about 8 to about 24 carbon atoms, x is from about 1 to about 10, and M is a water-soluble cation such as ammonium, magnesium, sodium, potassium, or triethanolamine. The alkyl ether sulfates are typically made as condensation products of ethylene oxide and monohydric alcohols having from about 8 to about 24 carbon atoms. Preferably, R has from about 10 to about 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with about 1 to about 10, preferably from about 2 to about 5, and more preferably with about 3, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the cleansing phase are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 10 to about 16 carbon atoms and an average degree of ethoxylation of from about 1 to about 4 moles of ethylene oxide.

Other suitable anionic surfactants include water-soluble salts of the organic, sulfuric acid reaction products of the general formula $[R^1—SO_3\text{-}M]$, wherein $R^1$ is chosen from the group consisting of a straight or branched chain, saturated aliphatic hydrocarbon radical having from about 8 to about 24, preferably from about 10 to about 18, carbon atoms; and M is a cation. Suitable examples are the salts of an organic sulfuric acid reaction product of a hydrocarbon of the methane series, including iso-, neo-, ineso-, and n-paraffins, having about 8 to about 24 carbon atoms, preferably about 10 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated $C_{10-18}$ n-paraffins.

Preferred anionic surfactants for use in the cleansing phase include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium tridecyl benzene sulfonate, sodium dodecyl benzene sulfonate, and combinations thereof.

Anionic surfactants with branched alkyl chains such as sodium trideceth sulfate, for example, are preferred in some embodiments. Mixtures of anionic surfactants can be used in some embodiments.

Amphoteric surfactants suitable for use as cleansing surfactant in the cleansing phase of the present compositions include those that are broadly described as derivatives of aliphatic secondary and tertiary amines in which the aliphatic radical can be straight or branched chain and wherein one of the aliphatic substituents contains from about 8 to about 18 carbon atoms and one contains an anionic group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378. Zwitterionic surfactants suitable for use as cleansing surfactant in the cleansing phase include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate.

Cationic surfactants can optionally be used in the cleansing phase, and preferably represent less than about 5%, by weight of the cleansing phase.

Nonionic surfactants for use in the compositions of the present invention are disclosed in McCutcheon's, Detergents and Emulsifiers, North American edition (1986), published by allured Publishing Corporation; and McCutcheon's, Functional Materials, North American Edition (1992).

Nonionic surfactants useful herein include those selected from the group consisting of alkyl glucosides, alkyl polyglucosides, polyhydroxy fatty acid amides, alkoxylated fatty acid esters, lathering sucrose esters, amine oxides, and mixtures thereof.

Non-limiting examples of preferred nonionic surfactants for use herein are those selected form the group consisting of $C_8$-$C_{14}$ glucose amides, $C_8$-$C_{14}$ alkyl polyglucosides (decyl polyglucoside) (APG 325, Henkel); lauryl polyglucoside (APG 600CS, Henkel), sucrose cocoate, sucrose laurate, and mixtures thereof. In a preferred embodiment the nonionic surfactant is selected from the group consisting of glyceryl monohydroxystearate, Steareth-2, hydroxy stearic acid, propylene glycol stearate, PEG-2 stearate, sorbitan monostearate, glyceryl stearate, laureth-2 and mixtures thereof. In a preferred embodiment the nonionic surfactant is Steareth-2.

Nonionic lathering surfactants also useful herein include, lauramine oxide, cocoamine oxide.

Other suitable non-ionic surfactants are Surfadone LP-100 and Surfadone LP-300 from International Specialty Products.

2. Thickener

The cleansing phase of the present invention comprises at least one thickener. Preferred thickeners are selected from the group consisting of inorganic water thickeners, polymeric thickeners, additives that promote thickening via lamellar structuring of surfactants, organic crystalline thickeners, and mixtures thereof.

The thickener in the present invention can be hydrophilic. The amount of thickener present may be less than about 20%, preferably less than about 10%, and even more preferably less than about 5%.

Non-limiting examples of inorganic water thickeners for use in the personal care composition include silicas, clays such as a synthetic silicates (Laponite XLG and Laponite XLS from Southern Clay), or mixtures thereof.

Non-limiting examples of polymeric thickeners for use in the personal care composition include Acrylates/Vinyl Isodecanoate Crosspolymer (Stabylen 30 from 3V), Acrylates/C10-30 Alkyl Acrylate Crosspolymer (Pemulen TR1 and TR2), Carbomers (Aqua SF-1), Ammonium Acryloyldimethyltaurate/VP Copolymer (Aristoflex AVC from Clariant), Ammonium Acryloyldimethyltaurate/Beheneth-25 Methacrylate Crosspolymer (Aristoflex HMB from Clariant), Acrylates/Ceteth-20 Itaconate Copolymer (Structure 3001 from National Starch), Polyacrylamide (Sepigel 305 from SEPPIC), Non-ionic thickener, (Aculyn 46 from Rohm and Haas), or mixtures thereof.

Additional non-limiting examples of polymeric thickeners for use in the personal care composition include cellulosic gel, hydroxypropyl starch phosphate (Structure XL from National Starch), polyvinyl alcohol, or mixtures thereof.

Further, non-limiting examples of polymeric thickeners for use in the personal care composition include synthetic and natural gums and thickeners such as xanthan gum (Ketrol CG-T from CP Kelco), succinoglycan (Rheozan from Rhodia), gellum gum, pectin, alginates, starches including pregelatinized starches, modified starches, or mixtures thereof, acrylates/aminoacrylates/CD-30 alkyl PEG-20 itaconate copolymer (Structure Plus from National Starch).

Non-limiting examples of additives that promote thickening via lamellar structuring of surfactants for use in the personal care composition include fatty amides, fatty alcohols, fatty acid or ester derivatives thereof, electrolytes, and mixtures thereof. Examples of fatty acids which may be used are $C_{10}$-$C_{22}$ acids such as the following: lauric acid, oleic acid, isostearic acid, linoleic acid, linolenic acid, ricinoleic acid, elaidic acid, arichidonic acid, myristoleic acid, palmitoleic acid, and the like. Ester derivatives include propylene glycol, isostearate, propylene glycol oleate, glyceryl isostearate, glyceryl oleate, polyglyceryl diisostearate, and the like.

Non-limiting examples of organic crystalline thickeners for use in the personal care composition include ethylene glycol esters of fatty acids preferably having from about 16 to about 22 carbon atoms. Other long chain acyl derivatives include long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin) a commercial example of which is Thixin R available from Rheox, Inc. Other suitable thickeners are alkyl (C16 to C22) dimethyl amide oxides such as stearyl dimethyl amine oxide. Also useful herein are long chain acyl derivatives, ethylene glycol esters of long chain carboxylic acids, long chain amine oxides, and alkanol amides of long chain carboxylic acids.

B. Benefit Phase

The personal care compositions of the present invention comprise at least one benefit phase. The benefit phase comprises at least one thickener and at least one benefit agent selected from the group consisting of styling polymers, silicones, crosslinked silicone elastomers, peralkylene hydrocarbons, and hair coloring agents/dyes. The benefit phase may further comprise benefit agents selected from the group consisting of anti-dandruff actives, humectants, water soluble nonionic polymers, cationic polymers, conditioning agents, and particles.

Benefit agents are useful in providing for enhanced perfume delivery, enhanced cleaning, hair coloring, hair styling, hair moisturizing, hair health enhancing, hair shine enhancing, hair volumizing, etc. Preferably, the benefit phase is present in an amount of from about 5% to about 95%, preferably from about 10% to about 90%, and more preferably from about 20% to about 80% by weight of the composition.

1. Thickener

The benefit phase of the personal care compositions comprises a thickener. Thickeners useful in the benefit phase are the same as those described in the cleansing phase section. The thickeners can be the same or different types and can be at the same levels or different levels in the two phases.

2. Benefit Agent

The compositions of the present invention comprise at least one benefit agent. Benefit agents are selected from the group consisting of styling polymers, silicones, crosslinked silicone elastomers, peralkylene hydrocarbons, and hair coloring agents/dyes. The benefit phase may further comprise benefit agents selected from the group consisting of anti-dandruff actives, humectants, water soluble nonionic polymers, cationic polymers, conditioning agents, and particles.

a. Styling Polymers

The compositions of the present invention may comprise a styling polymer. The compositions hereof will generally comprise from about 0.1% to about 15%, preferably from 0.5% to about 8%, more preferably from about 1% to about 8%, by weight of the composition, of the styling polymer. It is not intended to exclude the use of higher or lower levels of the polymers, as long as an effective amount is used to provide adhesive or film-forming properties to the composition and the composition can be formulated and effectively applied for its intended purpose.

These styling polymers provide the composition of the present invention with hair styling performance by providing polymeric deposits on the hair after application. The polymer deposited on the hair has adhesive and cohesive strength and delivers styling primarily by forming welds between hair fibers upon drying, as is understood by those skilled in the art.

Many such polymers are known in the art, including water-soluble and water-insoluble organic polymers and water-insoluble silicone-grafted polymers, all of which are suitable for use in the composition herein, provided that they also have the requisite features or characteristics described hereinafter. Such polymers can be made by conventional or otherwise known polymerization techniques well known in the art, an example of which includes free radical polymerization.

The styling polymer should have a weight average molecular weight of at least about 20,000, preferably greater than about 25,000, more preferably greater than about 30,000, most preferably greater than about 35,000. There is no upper limit for molecular weight except that which limits applicability of the invention for practical reasons, such as processing, aesthetic characteristics, ability to formulate, etc. In general, the weight average molecular weight will be less than about 10,000,000, more generally less than about 5,000,000, and typically less than about 2,000,000. Preferably, the weight average molecular weight will be between about 20,000 and about 2,000,000, more preferably between about 30,000 and about 1,000,000, and most preferably between about 40,000 and about 500,000.

Suitable silicone grafted polymers are also disclosed in EPO Application 90307528.1, published as EPO Application 0 408 311 A2 on Jan. 11, 1991, Hayama, et al., U.S. Pat. No. 5,061,481, issued Oct. 29, 1991, Suzuki et al., U.S. Pat. No. 5,106,609, Bolich et al., issued Apr. 21, 1992, U.S. Pat. No. 5,100,658, Bolich et al., issued Mar. 31, 1992, U.S. Pat. No. 5,100,657, Ansher-Jackson, et al., issued Mar. 31, 1992, U.S. Pat. No. 5,104,646, Bolich et al., issued Apr. 14, 1992, U.S.

Ser. No. 07/758,319, Bolich et al, filed Aug. 27, 1991, and U.S. Ser. No. 07/758,320, Torgerson et al., filed Aug. 27, 1991.

Suitable cationic polymers include Polyquaternium-4 (Celquat H-100; L200—supplier National Starch); Polyquaternium-10 (Celquat SC-240C; SC-230 M—supplier National Starch); (UCARE polymer series—JR-125, JR-400, LR-400, LR-30M, LK, supplier Amerchol); Polyquaternium-11 (Gafquat 734; 755N—supplier ISP); Polyquaternium-16 (Luviquat FC 370; FC550; FC905; HM-552 supplier by BASF); PVP/Dimethylaminoethylmethacrylate (Copolymer 845; 937; 958—-ISP supplier); Vinyl Caprolactam/PVP/Dimethylaminoethyl Methacrylate copolymer (Gaffix VC-713; H2 OLD EP-1—supplier ISP); Chitosan (Kytamer L; Kytamer PC—supplier Amerchol); Polyquaternium-7 (Merquat 550—supplier Calgon); Polyquaternium-18 (Mirapol AZ-1 supplied by Rhone-Poulenc); Polyquaternium-24 (Quatrisoft Polymer LM-200—supplier Amerchol); Polyquaternium-28 (Gafquat HS-100—supplier ISP); Polyquaternium-46 (Luviquat Hold—supplier BASF); and Chitosan Glycolate (Hydagen CMF; CMFP—supplier Henkel); Hydroxyethyl Cetyldimonium Phosphate (Luviquat Mono CP—supplier BASF); and Guar Hydroxylpropyl Trimonium Chloride (Jaguar C series-13S, -14S, -17, -162, -2000, Hi-CARE 1000—supplier Rhône-Poulenc).

Suitable amphoteric polymers include Octylacrylmide/Acrylates/Butylaminoethyl Methacrylate Copolymer (Amphomer 28-4910, Amphomer LV-71 28-4971, Lovocryl-47 28-4947—National Starch supplier), and Methacryloyl ethyl betaine/methacrylates copolymer (Diaformer series supplier Mitsubishi).

Polymers which are partially zwitterionic are also useful. They possess a positive charge over a broad range of pH but contain acidic groups which are only negatively charged at basic pH. The polymer is positively charged at lower pH and neutral (have both negative and positive charge) at higher pHs. The zwitterionic polymer may be selected from cellulose derivatives, wheat derivatives and chitin derivatives such as are known in the art. Nonlimiting examples of zwitterionic polymers useful herein include Polyquaternium-47 (Merquat 2001—supplier Calgon (a zwitterionic copolymer of acrylic acid, methacryl amido propyl trimethyl ammonium chloride, and methyl acrylate)); Carboxyl Butyl Chitosan (Chitolam NB/101—marketed by Pilot Chemical Company, developed by Lamberti); and Dicarboxyethyl Chitosan (N-[(3'-hydroxy-2',3'-dicarboxy)ethyl]-beta-D-(1,4)-glucosamine) (available from Amerchol as, e.g., CHITOLAM NB/101).

Useful nonionic polymers include PVP or Polyvinylpyrrolidone (PVP K-15, K-30, K-60, K-90, K-120—supplier ISP) (Luviskol K series 12, 17, 30, 60, 80, & 90—supplier BASF); PVP/VA (PVP/VA series S-630; 735, 635, 535, 335, 235—supplier ISP) (Luviskol VA); PVP/DMAPA acrylates copolymer (Styleze CC-10—supplier ISP); PVP/VA/Vinyl Propionate copolymer (Luviskol VAP 343 E, VAP 343 I, VAP 343 PM—supplier BASF); Hydroxylethyl Cellulose (Cellosize HEC—supplier Amerchol); and Hydroxylpropyl Guar Gum (Jaguar HP series-8, -60, -105, -120—supplier Rhône-Poulenc).

A wide variety of natural, semi-natural, and synthetic styling polymers are useful herein, see suitable styling polymers in encyclopedia of polymers and thickeners, Cosmetic & Toiletries, Volume 117, No. 12, December 2002, pages 67-120.

b. Silicones

The compositions of the present invention may comprise a silicone. The silicone is preferably an insoluble silicone conditioning agent. The silicone conditioning agent particles may comprise volatile silicone, non-volatile silicone, or combinations thereof. Preferred are non-volatile silicone conditioning agents. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

The concentration of the silicone conditioning agent typically ranges from about 0.01% to about 10%, preferably from about 0.1% to about 8%, more preferably from about 0.1% to about 5%, more preferably from about 0.2% to about 3%. Non-limiting examples of suitable silicone conditioning agents, and optional suspending agents for the silicone, are described in U.S. Reissue Pat. No. 34,584, U.S. Pat. Nos. 5,104,646, and 5,106,609. The silicone conditioning agents for use in the compositions of the present invention preferably have a viscosity, as measured at 25° C., from about 20 to about 2,000,000 centistokes ("csk"), more preferably from about 1,000 to about 1,800,000 csk, even more preferably from about 50,000 to about 1,500,000 csk, more preferably from about 100,000 to about 1,500,000 csk.

The dispersed silicone conditioning agent particles typically have a number average particle diameter ranging from about 0.01 µm to about 50 µm. For small particle application to hair, the number average particle diameters typically range from about 0.01 µm to about 4 µm, preferably from about 0.01 µm to about 2 µm, more preferably from about 0.01 µm to about 0.5 µm. For larger particle application to hair, the number average particle diameters typically range from about 4 µm to about 50 µm, preferably from about 6 µm to about 30 µm, more preferably from about 9 µm to about 20 µm, more preferably from about 12 µm to about 18 µm.

Background material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989).

Silicone fluids include silicone oils, which are flowable silicone materials having a viscosity, as measured at 25° C., less than 1,000,000 csk, preferably from about 5 csk to about 1,000,000 csk, more preferably from about 100 csk to about 600,000 csk. Suitable silicone oils for use in the compositions of the present invention include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

Silicone oils include polyalkyl or polyaryl siloxanes which conform to the following Formula (III):

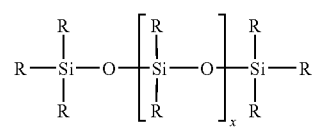

wherein R is aliphatic, preferably alkyl or alkenyl, or aryl, R can be substituted or unsubstituted, and x is an integer from 1 to about 8,000. Suitable R groups for use in the compositions of the present invention include, but are not limited to: alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

Preferred alkyl and alkenyl substituents are $C_1$ to $C_5$ alkyls and alkenyls, more preferably from $C_1$ to $C_4$, more preferably from $C_1$ to $C_2$. The aliphatic portions of other alkyl-, alkenyl-, or alkynyl-containing groups (such as alkoxy, alkaryl, and alkamino) can be straight or branched chains, and are preferably from $C_1$ to $C_5$, more preferably from $C_1$ to $C_4$, even more preferably from $C_1$ to $C_3$, more preferably from $C_1$ to $C_2$. As discussed above, the R substituents can also contain amino functionalities (e.g. alkamino groups), which can be primary, secondary or tertiary amines or quaternary ammonium. These include mono-, di- and tri-alkylamino and alkoxyamino groups, wherein the aliphatic portion chain length is preferably as described herein.

Cationic silicone fluids suitable for use in the compositions of the present invention include, but are not limited to, those which conform to the general formula (V):

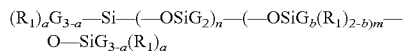

wherein G is hydrogen, phenyl, hydroxy, or $C_1$-$C_8$ alkyl, preferably methyl; a is 0 or an integer having a value from 1 to 3, preferably 0; b is 0 or 1, preferably 1; n is a number from 0 to 1,999, preferably from 49 to 499; m is an integer from 1 to 2,000, preferably from 1 to 10; the sum of n and m is a number from 1 to 2,000, preferably from 50 to 500; $R_1$ is a monovalent radical conforming to the general formula $C_qH_{2q}L$, wherein q is an integer having a value from 2 to 8 and L is selected from the following groups:

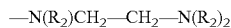

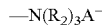

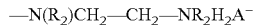

wherein $R_2$ is hydrogen, phenyl, benzyl, or a saturated hydrocarbon radical, preferably an alkyl radical from about $C_1$ to about $C_{20}$, and $A^-$ is a halide ion.

An especially preferred cationic silicone corresponding to formula (V) is the polymer known as "trimethylsilylamodimethicone", which is shown below in formula (VI):

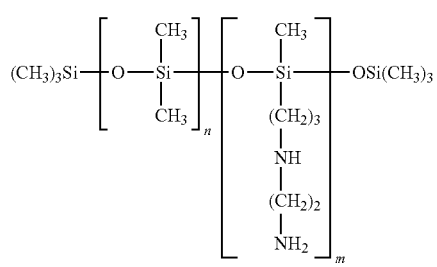

Other silicone cationic polymers which may be used in the compositions of the present invention are represented by the general formula (VII):

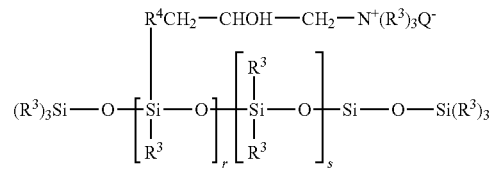

wherein $R^3$ is a monovalent hydrocarbon radical from $C_1$ to $C_{18}$, preferably an alkyl or alkenyl radical, such as methyl; $R_4$ is a hydrocarbon radical, preferably a $C_1$ to $C_{18}$ alkylene radical or a $C_{10}$ to $C_{18}$ alkyleneoxy radical, more preferably a $C_1$ to $C_8$ alkyleneoxy radical; $Q^-$ is a halide ion, preferably chloride; r is an average statistical value from 2 to 20, preferably from 2 to 8; s is an average statistical value from 20 to 200, preferably from 20 to 50. A preferred polymer of this class is known as UCARE SILICONE ALE 56™, available from Union Carbide.

Other silicone fluids suitable for use in the compositions of the present invention are the insoluble silicone gums. These gums are polyorganosiloxane materials having a viscosity, as measured at 25° C., of greater than or equal to 1,000,000 csk. Silicone gums are described in U.S. Pat. No. 4,152,416; Noll and Walter, *Chemistry and Technology of Silicones*, New York: Academic Press (1968); and in General Electric Silicone Rubber Product Data Sheets SE 30, SE 33, SE 54 and SE 76. Specific non-limiting examples of silicone gums for use in the compositions of the present invention include polydimethylsiloxane, (polydimethylsiloxane) (methylvinylsiloxane) copolymer, poly(dimethylsiloxane) (diphenyl siloxane) (methylvinylsiloxane) copolymer and mixtures thereof.

Other non-volatile, insoluble silicone fluid conditioning agents that are suitable for use in the compositions of the present invention are those known as "high refractive index silicones," having a refractive index of at least about 1.46, preferably at least about 1.48, more preferably at least about 1.52, more preferably at least about 1.55. The refractive index of the polysiloxane fluid will generally be less than about 1.70, typically less than about 1.60. In this context, polysiloxane "fluid" includes oils as well as gums.

The high refractive index polysiloxane fluid includes those represented by general Formula (III) above, as well as cyclic polysiloxanes such as those represented by Formula (VIII) below:

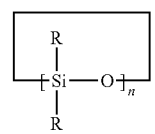

wherein R is as defined above, and n is a number from about 3 to about 7, preferably from about 3 to about 5.

The high refractive index polysiloxane fluids contain an amount of aryl-containing R substituents sufficient to increase the refractive index to the desired level, which is described herein. Additionally, R and n must be selected so that the material is non-volatile.

Aryl-containing substituents include those which contain alicyclic and heterocyclic five and six member aryl rings and those which contain fused five or six member rings. The aryl rings themselves can be substituted or unsubstituted.

Generally, the high refractive index polysiloxane fluids will have a degree of aryl-containing substituents of at least about 15%, preferably at least about 20%, more preferably at least about 25%, even more preferably at least about 35%, more preferably at least about 50%. Typically, the degree of aryl substitution will be less than about 90%, more generally less than about 85%, preferably from about 55% to about 80%.

Preferred high refractive index polysiloxane fluids have a combination of phenyl or phenyl derivative substituents (more preferably phenyl), with alkyl substituents, preferably $C_1$-$C_4$ alkyl (more preferably methyl), hydroxy, or $C_1$-$C_4$ alkylamino (especially —$R^1NHR^2NH2$ wherein each $R^1$ and $R^2$ independently is a $C_1$-$C_3$ alkyl, alkenyl, and/or alkoxy).

When high refractive index silicones are used in the compositions of the present invention, they are preferably used in solution with a spreading agent, such as a silicone resin or a surfactant, to reduce the surface tension by a sufficient amount to enhance spreading and thereby enhance the glossiness (subsequent to drying) of hair treated with the compositions.

Silicone fluids suitable for use in the compositions of the present invention are disclosed in U.S. Pat. Nos. 2,826,551, and 3,964,500, and 4,364,837, British Pat. No. 849,433, and *Silicon Compounds*, Petrarch Systems, Inc. (1984).

Silicone resins may be included in the silicone conditioning agent of the compositions of the present invention. These resins are highly cross-linked polymeric siloxane systems. The cross-linking is introduced through the incorporation of trifunctional and tetrafunctional silanes with monofunctional or difunctional, or both, silanes during manufacture of the silicone resin.

Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetra-functional unit $SiO_2$. Primes of the unit symbols (e.g. M', D', T', and Q') denote substituents other than methyl, and must be specifically defined for each occurrence.

Preferred silicone resins for use in the compositions of the present invention include, but are not limited to MQ, MT, MTQ, MDT and MDTQ resins. Methyl is a preferred silicone substituent. Especially preferred silicone resins are MQ resins, wherein the M:Q ratio is from about 0.5:1.0 to about 1.5:1.0 and the average molecular weight of the silicone resin is from about 1000 to about 10,000.

c. Crosslinked Silicone Elastomers

The personal care compositions of the present invention may comprise crosslinked silicone elastomers. Crosslinked silicone elastomers are present in an amount of from about 0.01% to about 15%, preferably from about 0.1% to about 10%, even more preferably from about 1% to about 5% by weight of the composition. These benefit agents provide hair alignment and softness (emollient) benefits to hair. Preferred compositions are dimethicone/vinyl dimethicone crosspolymers. Such dimethicone/vinyl dimethicone crosspolymers are supplied by a variety of suppliers including Dow Corning (DC 9040 and DC 9041), General Electric (SFE 839), Shin Etsu (KSG-15, 16, 18 [dimethicone/phenyl vinyl dimethicone crosspolymer]), Grant Industries (Gransil™ line of materials), and lauryl dimethicone/vinyl dimethicone crosspolymers supplied by Shin Etsu (e.g., KSG-31, KSG-32, KSG-41, KSG-42, KSG-43, and KSG-44). Cross-linked organopolysiloxane elastomers useful in the present invention and processes for making them are further described in U.S. Pat. Nos. 4,970,252; and 5,760,116; and 5,654,362; and Japanese Patent Application JP 61-18708, assigned to Pola Kasei Kogyo KK. Silicone elastomers of the type described in U.S. Pat. Nos. 5,412,004; 5,837,793; and 5,811,487, are also useful herein. Preferably the elastomers of the present invention are cured under anhydrous conditions or in an anhydrous environment.

d. Peralkylene Hydrocarbons

The present invention may include peraklylene hydrocarbon materials. These materials are a branched alk(en)yl material, of which the side-groups are —H, $C_{1-4}$ alk(en)yl groups or (—H or $C_{1-4}$ alk(en)yl) substituted saturated or unsaturated cyclic hydrocarbons, and wherein at least 10% by number of the side-groups are other than —H, more preferably from 25% to 75%, most preferably from 40% to 60%. Preferred alkyl side-groups are methyl groups.

Preferably the weight average molecular weight of the per-alk(en)yl hydrocarbon material is less than about 4200, preferably from about 180 to about 2500. Such low molecular weight per-alk(en)yl hydrocarbon materials are available for example from BP under the trade name Indopol, from Soltex under the tradename Solanes and from Chevron under the tradename Oronite OLOA.

It is also advantageous to control the particle size of the per-alk(en)yl hydrocarbon materials in order to maintain suitable conditioning characteristic of the composition. The combination of per-alk(en)yl hydrocarbon materials having a particle size from about 0.01μ to about 40μ and cationic deposition polymers, especially celluloses, allow for the conditioning aspects of the formula to be controlled and targeted towards a given consumer group. Through the use of low molecular weight per-alk(en)yl hydrocarbon materials, the need for large levels of expensive conditioning oils to mitigate the trade-offs traditionally associated with styling shampoos is significantly reduced.

Preferred per-alk(en)yl hydrocarbon materials are polymers of butene, isoprene, terpene and styrene, and copolymers of any combination of these monomers, such as butyl rubber (poly isobutylene-co-isoprene), natural rubber (cis-1, 4-polyisoprene) and hydrocarbon resins such as mentioned in the Encyclopedia of Chemical Technology by Kirk & Ohmer (3rd edition vol 8, pp 852-869), for example aliphatic and aromatic petroleum resins, terpene resins etc. Especially preferred is the use of polymers which are soluble in the low molecular weight per-alk(en)yl hydrocarbon material or other solvent or carrier, if used.

Especially preferred are per-alk(en)yl hydrocarbon materials of the formula:

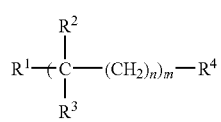

wherein:
n=0-3, preferably 1;
m=an integer such that the weight average molecular weight of the hydrocarbon is less than or equal to 4200.
$R^1$ is —H or a $C_{1-4}$ alkyl group; preferably methyl;
$R^2$ is a $C_{1-4}$ alkyl group; preferably methyl;

$R^3$ is —H or a $C_{1-4}$ alkyl group; preferably —H or methyl

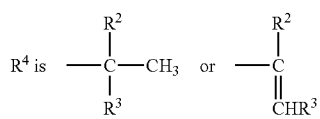

Especially preferred are polybutene materials of the formula:

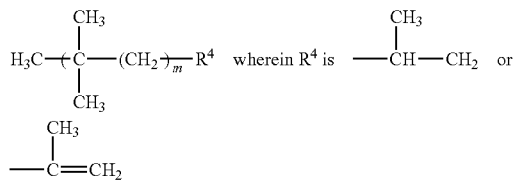

These materials are available from Presperse Inc. under the Permethyl trade name. The total level of per-alk(en)yl hydrocarbon material in the hair styling composition is preferably from about 0.01% to about 10%, more preferably from about 0.2% to about 5% even more preferably from about 0.2% to about 2% by weight of the composition.

e. Hair Coloring Agents/Dyes

The compositions of the present invention may also include hair coloring agents/dyes. Hair coloring agents/dyes useful herein include anthroquinone, azo, nitro, basic, triarylmethane, or disperse dyes, or any combinations thereof. A range of direct dyes, including basic dyes and neutral dyes are useful herein. Dyes suitable for use are described in U.S. Pat. Nos. 5,281,240 and 4,964,874.

f. Anti-Dandruff Actives

The compositions of the present invention may also contain an anti-dandruff agent. Suitable, non-limiting examples of anti-dandruff particulates include: pyridinethione salts, azoles, selenium sulfide, climbazole, particulate sulfur, and mixtures thereof. Preferred are pyridinethione salts. Such anti-dandruff particulate should be physically and chemically compatible with the essential components of the composition, and should not otherwise unduly impair product stability, aesthetics or performance.

Pyridinethione anti-dandruff particulates, especially 1-hydroxy-2-pyridinethione salts, are highly preferred particulate anti-dandruff agents for use in compositions of the present invention. The concentration of pyridinethione anti-dandruff particulate typically ranges from about 0.1% to about 4%, by weight of the composition, preferably from about 0.1% to about 3%, more preferably from about 0.3% to about 2%. Preferred pyridinethione salts include those formed from heavy metals such as zinc, tin, cadmium, magnesium, aluminum and zirconium, preferably zinc, more preferably the zinc salt of 1-hydroxy-2-pyridinethione (known as "zinc pyridinethione" or "ZPT"), more preferably 1-hydroxy-2-pyridinethione salts in platelet particle form, wherein the particles have an average size of up to about 20μ, preferably up to about 5μ, more preferably up to about 2.5μ. Salts formed from other cations, such as sodium, may also be suitable. Pyridinethione anti-dandruff agents are described, for example, in U.S. Pat. Nos. 2,809,971; 3,236,733; 3,753,196; 3,761,418; 4,345,080; 4,323,683; 4,379,753; and 4,470,982. It is contemplated that when ZPT is used as the anti-dandruff particulate in the compositions herein, that the growth or re-growth of hair may be stimulated or regulated, or both, or that hair loss may be reduced or inhibited, or that hair may appear thicker or fuller.

In addition to the anti-dandruff active selected from polyvalent metal salts of pyrithione, the present invention may further comprise one or more anti-fungal or anti-microbial actives in addition to the metal pyrithione salt actives. Suitable anti-microbial actives include coal tar, sulfur, whitfield's ointment, castellani's paint, aluminum chloride, gentian violet, octopirox (piroctone olamine), ciclopirox olamine, undecylenic acid and it's metal salts, potassium permanganate, selenium sulphide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone and azoles, and combinations thereof. Preferred anti-microbials include itraconazole, ketoconazole, selenium sulphide and coal tar.

Azole anti-microbials include imidazoles such as benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and triazoles such as terconazole and itraconazole, and combinations thereof. When present in the composition, the azole anti-microbial active is included in an amount from about 0.01% to about 5%, preferably from about 0.1% to about 3%, and more preferably from about 0.3% to about 2%, by weight of the composition. Especially preferred herein is ketoconazole.

Selenium sulfide is a particulate anti-dandruff agent suitable for use in the anti-microbial compositions of the present invention, effective concentrations of which range from about 0.1% to about 4%, by weight of the composition, preferably from about 0.3% to about 2.5%, more preferably from about 0.5% to about 1.5%. Selenium sulfide is generally regarded as a compound having one mole of selenium and two moles of sulfur, although it may also be a cyclic structure that conforms to the general formula $Se_xS_y$, wherein x+y=8. Average particle diameters for the selenium sulfide are typically less than 15 μm, as measured by forward laser light scattering device (e.g. Malvern 3600 instrument), preferably less than 10 μm. Selenium sulfide compounds are described, for example, in U.S. Pat. Nos. 2,694,668; 3,152,046; 4,089,945; and 4,885,107.

Sulfur may also be used as a particulate anti-microbial/anti-dandruff agent in the anti-microbial compositions of the present invention. Effective concentrations of the particulate sulfur are typically from about 1% to about 4%, by weight of the composition, preferably from about 2% to about 4%.

The present invention may further comprise one or more keratolytic agents such as Salicylic Acid.

Additional anti-microbial actives of the present invention may include extracts of melaleuca (tea tree) and charcoal. The present invention may also comprise combinations of anti-microbial actives. Such combinations may include octopirox and zinc pyrithione combinations, pine tar and sulfur combinations, salicylic acid and zinc pyrithione combinations, octopirox and climbasole combinations, and salicylic acid and octopirox combinations, and mixtures thereof.sulfur are typically from about 1% to about 4%, preferably from about 2% to about 4%.

g. Humectants

The compositions of the present invention may contain a humectant. The humectants herein are selected from the group consisting of polyhydric alcohols, water soluble alkoxylated nonionic polymers, and mixtures thereof. The humectants are preferably used at levels of from about 0.1% to about 20%, more preferably from about 0.5% to about 5%.

Polyhydric alcohols useful herein include glycerin, sorbitol, propylene glycol, butylene glycol, hexylene glycol, ethoxylated glucose, 1,2-hexane diol, hexanetriol, dipropylene glycol, erythritol, trehalose, diglycerin, xylitol, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof.

Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof.

h. Water Soluble Nonionic Polymers

The compositions of the present invention may comprise from about 0.1% to about 10%, more preferably from about 0.2% to about 5%, and even more preferably from about 0.5% to about 3% by weight of a water soluble nonionic polymer.

The polymers of the present invention are characterized by the general formula:

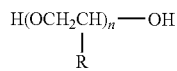

wherein R is selected from the group consisting of H, methyl, and mixtures thereof. When R is H, these materials are polymers of ethylene oxide, which are also known as polyethylene oxides, polyoxyethylenes, and polyethylene glycols. When R is methyl, these materials are polymers of propylene oxide, which are also known as polypropylene oxides, polyoxypropylenes, and polypropylene glycols. When R is methyl, it is also understood that various positional isomers of the resulting polymers can exist. In the above structure, n has an average value of from about 2,000 to about 14,000, preferably from about 5,000 to about 9,000, more preferably from about 6,000 to about 8,000.

Polyethylene glycol polymers useful herein that are especially preferred are PEG-2M wherein R equals H and n has an average value of about 2,000 (PEG 2-M is also known as Polyox WSR® N-10 from Union Carbide and as PEG-2,000); PEG-5M wherein R equals H and n has an average value of about 5,000 (PEG 5-M is also known as Polyox WSR® N-35 and Polyox WSR® N-80, both from Union Carbide and as PEG-5,000 and Polyethylene Glycol 300,000); PEG-7M wherein R equals H and n has an average value of about 7,000 (PEG 7-M is also known as Polyox WSR® N-750 from Union Carbide); PEG-9M wherein R equals H and n has an average value of about 9,000 (PEG 9-M is also known as Polyox WSR® N-3333 from Union Carbide); and PEG-14 M wherein R equals H and n has an average value of about 14,000 (PEG 14-M is also known as Polyox WSR® N-3000 from Union Carbide.) Other useful polymers include the polypropylene glycols and mixed polyethylene/polypropylene glycols.

i. Cationic Polymers

The compositions of the present invention may contain a cationic polymer. Concentrations of the cationic polymer in the composition typically range from about 0.05% to about 3%, preferably from about 0.075% to about 2.0%, more preferably from about 0.1% to about 1.0%. Preferred cationic polymers will have cationic charge densities of at least about 0.7 meq/gm, preferably at least about 1.2 meq/gm, more preferably at least about 1.5 meq/gm, but also preferably less than about 7 meq/gm, more preferably less than about 5 meq/gm, at the pH of intended use of the composition, which pH will generally range from about pH 3 to about pH 9, preferably between about pH 4 and about pH 8. Herein, "cationic charge density" of a polymer refers to the ratio of the number of positive charges on the polymer to the molecular weight of the polymer. The average molecular weight of such suitable cationic polymers will generally be between about 10,000 and 10 million, preferably between about 50,000 and about 5 million, more preferably between about 100,000 and about 3 million.

Suitable cationic polymers for use in the compositions of the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the composition. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Non limiting examples of such counterions include halides (e.g., chloride, fluoride, bromide, iodide), sulfate and methylsulfate.

Non limiting examples of such polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)).

Non limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Suitable cationic protonated amino and quaternary ammonium monomers, for inclusion in the cationic polymers of the composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polymers for use in the compositions include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16); copolymers of 1-vinyl-2-pyrrolidone and dimethylaminoethyl methacrylate (referred to in the industry by CTFA as Polyquaternium-11); cationic diallyl quaternary ammonium-containing polymers, including, for example, dimethyldiallylammonium chloride homopolymer, copolymers of acrylamide and dimethyldiallylammonium chloride (referred to in the industry by CTFA as Polyquaternium 6 and Polyquaternium 7, respectively); amphoteric copolymers of acrylic acid including copolymers of acrylic acid and dimethyldiallylammonium chloride (referred to in the industry by CTFA as Polyquaternium 22), terpolymers of acrylic acid with dimethyldiallylammonium chloride and acrylamide (referred to in the industry by CTFA as Polyquaternium 39), and terpolymers of acrylic acid with methacrylamidopropyl trimethylammonium chloride and methylacrylate (referred to in the industry by CTFA as Polyquaternium 47). Preferred cationic substituted monomers are the cationic substituted dialkylaminoalkyl acrylamides, dialkylaminoalkyl methacrylamides, and combinations thereof. These preferred monomers conform the to the formula

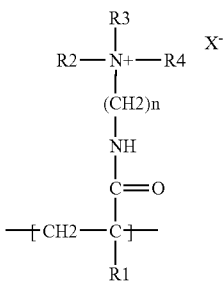

wherein $R^1$ is hydrogen, methyl or ethyl; each of $R^2$, $R^3$ and $R^4$ are independently hydrogen or a short chain alkyl having from about 1 to about 8 carbon atoms, preferably from about 1 to about 5 carbon atoms, more preferably from about 1 to about 2 carbon atoms; n is an integer having a value of from about 1 to about 8, preferably from about 1 to about 4; and X is a counterion. The nitrogen attached to $R^2$, $R^3$ and $R^4$ may be a protonated amine (primary, secondary or tertiary), but is preferably a quaternary ammonium wherein each of $R^2$, $R^3$ and $R^4$ are alkyl groups a non limiting example of which is polymethyacrylamidopropyl trimonium chloride, available under the trade name Polycare 133, from Rhone-Poulenc, Cranberry, N.J., U.S.A.

Other suitable cationic polymers for use in the composition include polysaccharide polymers, such as cationic cellulose derivatives and cationic starch derivatives. Suitable cationic polysaccharide polymers include those which conform to the formula

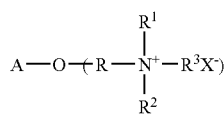

wherein A is an anhydroglucose residual group, such as a starch or cellulose anhydroglucose residual; R is an alkylene oxyalkylene, polyoxyalkylene, or hydroxyalkylene group, or combination thereof; R1, R2, and R3 independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R1, R2 and R3) preferably being about 20 or less; and X is an anionic counterion as described in hereinbefore.

Preferred cationic cellulose polymers are salts of hydroxyethyl cellulose reacted with trimethyl ammonium substituted epoxide, referred to in the industry (CTFA) as Polyquaternium 10 and available from Amerchol Corp. (Edison, N.J., USA) in their Polymer LR, JR, and KG series of polymers. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Amerchol Corp. under the tradename Polymer LM-200.

Other suitable cationic polymers include cationic guar gum derivatives, such as guar hydroxypropyltrimonium chloride, specific examples of which include the Jaguar series commercially available from Rhone-Poulenc Incorporated and the N-Hance series commercially available from Aqualon Division of Hercules, Inc. Other suitable cationic polymers include quaternary nitrogen-containing cellulose ethers, some examples of which are described in U.S. Pat. No. 3,962,418. Other suitable cationic polymers include copolymers of etherified cellulose, guar and starch, some examples of which are described in U.S. Pat. No. 3,958,581. When used, the cationic polymers herein are either soluble in the composition or are soluble in a complex coacervate phase in the composition formed by the cationic polymer and the anionic, amphoteric and/or zwitterionic detersive surfactant component described hereinbefore. Complex coacervates of the cationic polymer can also be formed with other charged materials in the composition.

Techniques for analysis of formation of complex coacervates are known in the art. For example, microscopic analyses of the compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the composition.

j. Conditioning Agents

Conditioning agents include any material which is used to give a particular conditioning benefit to hair and/or skin. Suitable conditioning agents for use in the composition include the previously mentioned silicones and peralkylene hydrocarbons as well as organic conditioning oils (e.g., hydrocarbon oils, polyolefins, and fatty esters) or combinations thereof.

The conditioning component of the compositions of the present invention may comprise from about 0.05% to about 3%, preferably from about 0.08% to about 1.5%, more preferably from about 0.1% to about 1%, of at least one organic conditioning oil as the conditioning agent, either alone or in combination with other conditioning agents, such as the silicones (described herein).

Suitable organic conditioning oils for use as conditioning agents in the compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about $C_{12}$ to about $C_{19}$. Branched chain hydrocarbon oils, including hydrocarbon polymers, typically will contain more than 19 carbon atoms.

Organic conditioning oils for use in the compositions of the present invention can also include liquid polyolefins, more preferably liquid poly-α-olefins, more preferably hydrogenated liquid poly-α-olefins. Polyolefins for use herein are prepared by polymerization of $C_4$ to about $C_{14}$ olefenic monomers, preferably from about $C_6$ to about $C_{12}$.

Other suitable organic conditioning oils for use as the conditioning agent in the compositions of the present invention include, but are not limited to, fatty esters having at least 10 carbon atoms. These fatty esters include esters with hydrocarbyl chains derived from fatty acids or alcohols (e.g. monoesters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

Also suitable for use in the compositions herein are the conditioning agents described by the Procter & Gamble Company in U.S. Pat. Nos. 5,674,478, and 5,750,122. Also suitable for use herein are those conditioning agents described in U.S. Pat. No. 4,529,586 (Clairol), U.S. Pat. No. 4,507,280 (Clairol), U.S. Pat. No. 4,663,158 (Clairol), U.S. Pat. No. 4,197,865 (L'Oreal), U.S. Pat. No. 4,217,914 (L'Oreal), U.S. Pat. No. 4,381,919 (L'Oreal), and U.S. Pat. No. 4,422,853 (L'Oreal).

k. Particles

The personal care composition of the present invention may comprise particles. Water insoluble solid particle of various shapes and densities is useful. The particle of the present invention has a particle size (volume average based on the particle size measurement described hereafter) of less than about 100 μm, preferably less than about 60 μm, and more preferably the particle size of less than about 30 μm.

The particles that can be present in the present invention can be natural, synthetic, or semi-synthetic. In addition, hybrid particles can also be present. Synthetic particles can made of either cross-linked or non cross-linked polymers. The particles of the present invention can have surface charges or their surface can be modified with organic or inorganic materials such as surfactants, polymers, and inorganic materials. Particle complexes can be present.

Nonlimiting examples of synthetic particles include nylon, silicone resins, poly(meth)acrylates, polyethylene, polyester, polypropylene, polystyrene, polyurethane, polyamide, epoxy resins, urea resins, and acrylic powders. Non limiting examples of useful particles are Microease 110S, 114S, 116 (micronized synthetic waxes), Micropoly 210, 250S (micronized polyethylene), Microslip (micronized polytetrafluoroethylene), and Microsilk (combination of polyethylene and polytetrafluoroethylene), all of which are available from Micro Powder, Inc. Additional examples include Luna (smooth silica particles) particles available from Phenomenex, MP-2200 (polymethylmethacrylate), EA-209 (ethylene/acrylate copolymer), SP-501(nylon-12), ES-830 (polymethly methacrylate), BPD-800, BPD-500 (polyurethane) particles available from Kobo Products, Inc. and silicone resins sold under the name Tospearl particles by GE Silicones. Ganzpearl GS-0605 crosslinked polystyrene (available from Presperse) is also useful.

Non limiting examples of hybrid particles include Ganzpearl GSC-30SR (Sericite & crosslinked polystyrene hybrid powder), and SM-1000, SM-200 (mica and silica hybrid powder available from Presperse).

The interference pigments of the present invention are platelet particulates. The platelet particulates of the multi-phased personal care compositions preferably have a thickness of no more than about 5 μm, more preferably no more than about 2 μm, still more preferably no more than about 1 μm. The platelet particulates of the multi-phased personal care composition preferably have a thickness of at least about 0.02 μm, more preferably at least about 0.05 μm, even more preferably at least about 0.1 μm, and still more preferably at least about 0.2 μm.

The interference pigment of the multi-phased personal care compositions comprise a multilayer structure. The centre of the particulates is a flat substrate with a refractive index (RI) normally below 1.8. A wide variety of particle substrates are useful herein. Nonlimiting examples are natural mica, synthetic mica, graphite, talc, kaolin, alumina flake, bismuth oxychloride, silica flake, glass flake, ceramics, titanium dioxide, $CaSO_4$, $CaCO_3$, $BaSO_4$, borosilicate and mixtures thereof, preferably mica, silica and alumina flakes.

A layer of thin film or a multiple layer of thin films are coated on the surface of a substrate described above. The thin films are made of highly refractive materials. The refractive index of these materials is normally above 1.8.

A wide variety of thin films are useful herein. Nonlimiting examples are $TiO_2$, $Fe_2O_3$, $SnO_2$, $Cr_2O_3$, ZnO, ZnS, ZnO, SnO, $ZrO_2$, $CaF_2$, $Al_2O_3$, BiOCl, and mixtures thereof or in the form of separate layers, preferably $TiO_2$, $Fe_2O_3$, $Cr_2O_3SnO_2$. For the multiple layer structures, the thin films can be consisted of all high refractive index materials or alternation of thin films with high and low RI materials with the high RI film as the top layer.

Nonlimiting examples of the interference pigments useful herein include those supplied by Persperse, Inc. under the trade name PRESTIGE®, FLONAC®; supplied by EMD Chemicals, Inc. under the trade name TIMIRON®, COLORONA®, DICHRONA® and XIRONA®; and supplied by Engelhard Co. under the trade name FLAMENCO®, TIMICA®, DUOCHROME®.

In an embodiment of the present invention the interference pigment surface is either hydrophobic or has been hydrophobically modified. The Particle Contact Angle Test as described in copending application Ser. No. 60/469,075 filed on May 8, 2003 is used to determine contact angle of interference pigments. The greater the contact angle, the greater the hydrophobicity of the interference pigment. The interference pigment of the present invention possess a contact angle of at least 60 degrees, more preferably greater than 80 degrees, even more preferably greater than 100 degrees, still more preferably greater than 100 degrees.

Nonlimiting examples of the hydrophobic surface treatment useful herein include silicones, acrylate silicone copolymers, acrylate polymers, alkyl silane, isopropyl titanium triisostearate, sodium stearate, magnesium myristate, perfluoroalcohol phosphate, perfluoropolymethyl isopropyl ether, lecithin, carnauba wax, polyethylene, chitosan, lauroyl lysine, plant lipid extracts and mixtures thereof, preferably, silicones, silanes and stearates. Surface treatment houses include US Cosmetics, KOBO Products Inc., and Cardre Inc.

3. Other Ingredients

The benefit phase may optionally comprise any component listed in the cleansing phase section herein or any component listed in the optional ingredient section herein. When the benefit phase comprises a surfactant described herein, the surfactant is selected from the group consisting of anionic surfactants, nonionic surfactants, zwitterionic surfactants, amphoteric surfactants, and mixtures thereof. The surfactant may optionally be selected from the group consisting of nonionic surfactants, zwitterionic surfactants, amphoteric surfactants, and mixtures thereof. The surfactant may be present in an amount of from about 1% to about 50%, more preferably from about 4% to about 30%, even more preferably from about 5% to about 25%, by weight of the benefit phase. The surfactant may be present in an amount of at least 8% by weight of composition of said benefit phase.

C. Aqueous Carrier

The compositions of the present invention may comprise an aqueous carrier. The aqueous carrier may be found in the cleansing phase, the benefit phase, or both the cleansing phase and the benefit phase. Preferably, they comprise from about 50% to about 99.8%, by weight of water. The aqueous carrier can optionally include other liquid, water-miscible or water-soluble solvents such as lower alkyl alcohols, e.g. $C_1$-$C_5$ alkyl monohydric alcohols, preferably $C_2$-$C_3$ alkyl alcohols.

D. Optional Ingredients

The compositions herein can contain a variety of other optional components suitable for rendering such compositions more cosmetically or aesthetically acceptable or to provide them with additional usage benefits. Optional ingredients may be found in either the cleansing phase or the benefit phase. Such conventional optional ingredients are well-known to those skilled in the art.

A wide variety of additional ingredients can be formulated into the present composition. These include: other conditioning agents; viscosity modifiers such as alkanolamides and methanolamides of long chain fatty acids such as cocomonoethanol amide; crystalline suspending agents; pearlescent aids such as ethylene glycol distearate; preservatives such as benzyl alcohol, methyl paraben, propyl paraben and imidazolidinyl urea; polyvinyl alcohol; ethyl alcohol; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; hair oxidizing (bleaching) agents, such as hydrogen peroxide, perborate and persulfate salts; hair reducing agents, such as the thioglycolates; perfumes; sequestering agents, such as disodium ethylenediamine tetra-acetate; and polymer plasticizing agents, such as glycerin, disobutyl adipate, butyl stearate, and propylene glycol. Other non limiting examples of these optional ingredients include vitamins and derivatives thereof (e.g., ascorbic acid, vitamin E, tocopheryl acetate, and the like); sunscreens; thickening agents (e.g., polyol alkoxy ester, available as Crothix from Croda); preservatives for maintaining the anti microbial integrity of the cleansing compositions; anti-acne medicaments (resorcinol, salicylic acid, and the like); antioxidants; skin soothing and healing agents such as aloe vera extract, allantoin and the like; chelators and sequestrants; and agents suitable for aesthetic purposes such as fragrances, essential oils, skin sensates, pigments, pearlescent agents (e.g., mica and titanium dioxide), lakes, colorings, and the like (e.g., clove oil, menthol, camphor, eucalyptus oil, and eugenol).

Other optional hair and skin benefit ingredients include carboxylic acid which is hydroxylated in the α position (which compound is also referred to as an α-(alpha) hydroxyl acid) or a derivative thereof. Acid derivatives, as defined herein, are associated salts (salts with organic bases or alkali metal, for example) or lactides (obtained, for example, by autiesterification of α-hydroxy acid molecules). Examples of such compounds are, citric acid, lactic acid, methallactic acid, phenyllactic acid, malic acid, mandelic acid, glycolic acid, benzylic acid, and 2-hydroxycaprylic acid.

Additional hair and skin benefit agents include ceramides or glycoceramides. Ceramides are described in Arch. Dermatol, Vol 123, 1381-1384, 1987, or those described in French Patent FR-2,673,179; fatty acid polyesters such as, sucrose pentalaurate, sucrose tetraoleate, sucrose pentaerucate, sucrose tetraerucate, sucrose pentatallowate, sucrise triapeate, sucrose tetrapeate, sucrose pentarapeate, sucrose tristearate, and sucrose pentastearate, and mixtures thereof; polypeptides and amino acids consisting of basic amino acids, particularly arginine.

The compositions optionally comprise a colorant or pigment. Preferably, the colorant comprises metal ions. Preferably, the colorant is free of barium and aluminum ions which allows for improved lamellar phase stability. The colorant preferably maintains UV stability.

The colorants for use in the compositions are selected from the group consisting of organic pigments, inorganic pigments, interference pigments, lakes, natural colorants, pearlescent agents, dyes (including, e.g., water soluble, non-soluble, oil-soluble), carmines, and mixtures thereof. Non-limiting examples of colorants include: D&C Red 30 Talc Lake, D&C Red 7 Calcium Lake, D&C Red 34 Calcium Lake, Mica/Titanium Dioxide/Carmine Pigments (Clorisonne Red from Engelhard, Duocrome RB from Engelhard, Magenta from Rona, Dichrona RB from Rona), Red 30 Low Iron, D&C Red Lake Blend of Lake 27 & Lake 30, FD&C Yellow 5 Lake, Kowet Titanium Dioxide, Yellow Iron Oxide, D&C Red 30 Lake, D&C Red 28 Lake, Cos Red Oxide BC, Cos Iron Oxide Red BC, Cos Iron oxide Black BC, Cos Iron Oxide Yellow, Cos Iron Oxide Brown, Cos Iron Oxide Yellow BC, Euroxide Red Unsteril, Euroxide Black Unsteril, Euroxide Yellow Steril, Euroxide Black Steril, Euroxide Red, Euroxide Black, Hydrophobic Euroxide Black, Hydrophobic Euroxide Yellow, Hydrophobic Euroxide Red, D&C Yellow 6 Lake, D&C Yellow 5 Zr Lake, Blue # 1, Orange # 4, Red # 4, Yellow # 5, and mixtures of these colorants.

Density Matching

To further improve stability under stress conditions such as high temperature and vibration, it is preferable to adjust the densities of the separate phases such that they are substantially equal. This is known as density matching. To achieve density matching, low density microspheres may be added to the denser phase of the composition. The low density microspheres employed to reduce the overall density of the cleansing phase are particles having a density lower than about 0.7 g/cm$^3$, preferably less than about 0.2 g/cm$^3$, more preferably less than about 0.1 g/cm$^3$, even more preferably less than about 0.05 g/cm$^3$. The low density microspheres generally have a diameter less than about 200 μm, preferably less than about 100 μm, even more preferably less than about 40 μm. Preferably, the density difference between the cleansing phase and the benefit phase is less than about 0.30 g/cm$^3$, preferably less than about 0.15 g/cm$^3$, more preferably, the density difference is less than about 0.10 g/cm$^3$, even more preferably, the density difference is less than about 0.05 g/cm$^3$, and even more preferably, the density difference is less than about 0.01 g/cm$^3$.

The microspheres are produced from any appropriate inorganic or organic material compatible with a use on the skin that is nonirritating and nontoxic.

Expanded microspheres made of thermoplastic material are known, and may be obtained, for example, according to the processes described in patents and patent applications EP-56219, EP-348372, EP-486080, EP-320473, EP-112807 and U.S. Pat. No. 3,615,972.

The internal cavity of expanded hollow microspheres contains a gas, which can be a hydrocarbon such as isobutane or isopentane or alternatively air. Among hollow microspheres which can be used, special mention may be made of those marketed under the brand name EXPANCEL® (thermoplastic expandable microspheres) by the Akzo Nobel Company, especially those of DE (dry state) or WE (hydrated state) grade. Examples include: Expancel® 091 DE 40 d30; Expancel® 091 DE 80 d30; Expancel® 051 DE 40 d60; Expancel® 091 WE 40 d24; Expancel® 053 DE 40 d20.

Representative microspheres derived from an inorganic material, include, for instance, "Qcel® Hollow Microspheres" and "EXTENDOSPHERES™ Ceramic Hollow Spheres", both available from the PQ Corporation. Examples are: Qcel® 300; Qcel® 6019; Qcel® 6042S.

Just as low density microspheres can be added to the denser phase of the present invention to improve vibrational stability, high density materials can be added to the less dense phase to increase its density having the same impact on stability.

The density of each phase is measured by a Pycnometer. Density is calculated in $g/cm^3$. In matching densities, the densities of the two phases must not be substantially different and should preferably be within a range of +/−15%, more preferably within a range of +/−10%, even more preferably within a range of +/−5%.

Method of Use

The personal care compositions of the present invention are used in conventional ways to provide cleansing and other benefits. Such method of use depends upon the type of composition employed but generally involves application of an effective amount of the product to the hair or skin, which may then be rinsed from the hair or skin (as in the case of hair rinses) or allowed to remain on the hair or skin (as in the case of gels, lotions, and creams). "Effective amount" means an amount sufficient enough to provide a dry combing benefit. In general, from about 1 g to about 50 g is applied to the hair, skin, or the scalp. The composition is distributed throughout the hair or skin, typically by rubbing or massaging the hair, scalp, or skin. Preferably, the composition is applied to wet or damp hair prior to drying of the hair. The composition may optionally be applied via a substrate. After such compositions are applied to the hair, the hair is dried and styled in accordance with the preference of the user. In the alternative, the composition is applied to dry hair, and the hair is then combed or styled in accordance with the preference of the user. The personal care compositions are useful in delivering conditioning benefits to hair or skin, and/or delivering hair styling benefits to hair or skin, and/or delivering hair coloring benefits to hair or skin by topically applying an effective amount of the composition onto hair or skin and rinsing said hair or skin with water. For some applications, the rinsing step can be optional.

Method of Making

The personal care compositions of the present invention may be prepared by any known or otherwise effective technique, suitable for making and formulating the desired product form. It is especially effective to combine toothpaste-tube filling technology with a spinning stage design. Specific non-limiting examples of such methods as they are applied to specific embodiments of the present invention are described in the following examples.

NON-LIMITING EXAMPLES

The compositions illustrated in the following Examples exemplify specific embodiments of the compositions of the present invention, but are not intended to be limiting thereof. Other modifications can be undertaken by the skilled artisan without departing from the spirit and scope of this invention. The cleansing phase and the benefit phase are prepared separately.

The compositions illustrated in the following Examples are prepared by conventional formulation and mixing methods, an example of which is described above. All exemplified amounts are listed as weight percents and exclude minor materials such as diluents, preservatives, color solutions, imagery or conceptual ingredients, botanicals, and so forth, unless otherwise specified.

Examples 1-3

|  | Example 1 | Example 2 | Example 3 |
| --- | --- | --- | --- |
| Cleansing Phase Composition | | | |
| Sodium Laureth-3 Sulfate (AES, 28%) (Procter &Gamble Chemicals) | 14.3 | 17.8 | 14.3 |
| Sodium Lauryl Sulfate (ALS, 29%) (Procter &Gamble Chemicals) | 40.9 | 51 | 40.9 |
| Cocamidopropyl Betaine (CAPB, 30%) (Goldschmidt Chemical) | 5.3 | 42 | 13.3 |
| Coconutmonoethanol amide (CMEA, Mona Industries) | 2.0 | 3 | 2.0 |
| C10-C16 Alkyldimethyl amine oxide (32%) (AO, Procter &Gamble Chemicals) | 7.5 | — | — |
| Guar Hydroxypropyltrimonium Chloride (N-Hance 3196 from Aqualon) | 0.5 | — | — |
| Cetyl alcohol | — | 0.5 | — |
| Carbopol Aqua SF-1 (Noveon) | — | 3.3 | — |
| Polyquaterium 10 (UCARE polymer JR-30M from Amerchol) | — | 0.45 | — |
| Polymethacrylamidopropyltrimonium Chloride (Polycare 133 from Rhodia) | 0.5 | — | — |
| Dimethicone (Viscasil 330M from General Electric) | 4.2 | — | — |
| Lithium magnesium silicate (Laponite XLS from Southern Clay) | — | — | 0.5 |
| Ethylene Glycol Distearate (EGDS) | 1.5 | 1.5 | 1.5 |
| DMDM Hydantoin (Lonza) (55%) | 0.67 | 0.6 | — |
| D&C Red#30 Talc Lake | 0.05 | 0.05 | — |
| Citric Acid (Hoffman-Laroche) | 1.25 | — | 0.5 |
| Disodium EDTA (Dissolvine NA-2S, Akzo Nobel) | 0.05 | 0.05 | 0.04 |
| Perfume | 0.25 | 0.3 | 0.2 |
| Water | q.s. | q.s. | q.s. |
| Benefit Phase Compositions | | | |
| Cocamidopropyl Betaine (30%) (Goldschmidt Chemical) | 15 | 10 | 12 |
| C10-C16 Alkyldimethyl amine oxide (32%) (Procter &Gamble Chemicals) | — | 2 | 2 |
| Coconutmonoethanol amide (Mona Industries) | 2.0 | — | 2.0 |
| Crosslinked acrylic acid-vinyl ester copolymer (Satbylen 30 from 3V) | 1.0 | — | — |
| Carbopol Aqua SF-1 (30%) (Noveon) | — | 3.3 | 3.3 |
| Xanthan gum (Keltrol CGT from Kelco) | 1.1 | 0.75 | — |
| DMDM Hydantoin (Lonza) (55%) | 0.67 | 0.6 | — |
| Sodium chloride (Morton) | 3.0 | — | — |
| Dimethicone (Viscasil 330M from General Electric) | — | — | 3.3 |
| Basic Brown Dye 17/Cl 12251 (Arianor Sienna Brown) | — | 0.4 | — |
| Perfume | 0.2 | 0.2 | 0.15 |
| Triethanolamine (Dow Chemical) | 1.0 | q.s. to pH 6.5 | q.s. to pH 6.5 |
| Mica | — | — | 0.1 |
| Water | q.s. | q.s. | q.s. |
| Ratio Cleansing Phase/Benefit Phase | 60/40 | 60/40 | 70/30 |

Cleansing Phase Compositions:

In an appropriate vessel, add distilled water and stir at an appropriate speed (100-200 ppm) using an appropriate sized stir blade. If needed, add the anionic polymer (Carbopol Aqua SF-1), or cationic polymers (N-Hance 3196, Polyquaternium-10, Polycare 133) and stir briefly and slowly to wet and disperse the polymer. While continuing to stir, if needed, add the citiric acid solution (50%) drop wise to the mix vessel to reduce pH until solution becomes clear. Add surfactants (AS, AES, CAPB, and AO) to the mixture. Heat the mixture to 60° C. and while stirring add CMEA, EGDS, and Cetyl alcohol to the mixture. Mix until homogeneous. Cool the solution to room temperature while stirring and add Dimethicone, EDTA, Mackstat DM-C, D&C pigment, and perfume. Finally, adjust pH of the product within the preferred specified range of from about 5.5 to about 6.5. Where required, Laponite XLS is added to the solution (heated to 40° C.) and the solution is heated to 60-65° C. prior to the addition of surfactants.

Benefit Phase Compositions:

Into an appropriately sized and cleaned vessel, add distilled water and stir at 200-300 rpm by using an appropriate laboratory stirrer. Slowly add Stabylen 30 and mix until homogeneous. Weigh the appropriate quantity of Keltrol CGT and slowly add it to the mix. Stir until homogeneous. Into a second vessel add surfactants (CAPB, AO) and begin stirring and heating to 60° C. After stirring briefly, add CMEA. Add the phase containing Stabylen 30 and Keltrol CGT to the surfactant phase. Add Triethanolamine while stirring. Add remaining ingredients and adjust pH within the specified range of from about 5.5 to about 6.5.

Density Matching of Phases:

Density match the cleansing and benefit phases within 0.05 g/cm$^3$. Combine these phases by first placing the separate phases in separate storage tanks having a pump and a hose attached. Then, pump the phases in predetermined amounts into a single combining section. Next, move the phases from the combining sections into blending sections and mix the phases in the blending section such that the single resulting product exhibits a distinct pattern of phases. Next, pump the product that was mixed in the blending section via a hose into a single nozzle into a spinning container, and fill the container from the bottom to the top with the resulting product.

Examples 4-6

|  | Example 4 | Example 5 | Example 6 |
|---|---|---|---|
| Cleansing Phase Composition |  |  |  |
| Sodium Laureth-3 Sulfate (28%) (Procter &Gamble Chemicals) | 14.3 | 14.3 | 14.3 |
| Sodium Lauryl Sulfate (29%) (Procter &Gamble Chemicals) | 40.9 | 40.9 | 40.9 |
| Cocamidopropyl Betaine (30%) (Goldschmidt Chemical) | 13.3 | 13.3 | 13.3 |
| Coconutmonoethanol amide (Mona Industries) | 2.0 | 2.0 | 2.0 |
| Lauryl Pyrrolidone (Surfadone LP-300, ISP Industries) | 1.0 | 1.0 | 1.0 |
| Carbopol Aqua SF-1 (Noveon) | — | 1.7 | 1.7 |
| Triethanolamine | — | 0.76 | 0.76 |
| Dimethicone (Viscasil 330M from General Electric) | 4.2 | 6.0 | — |
| Lithium magnesium silicate (Laponite XLS from Southern Clay) | — | — | 1.0 |
| Ethylene Glycol Distearate | 1.5 | — | 1.5 |
| DMDM Hydantoin (Lonza) (55%) | 0.7 | 0.6 | — |
| D&C Red#30 Talc Lake | — | 0.05 | — |
| Citric Acid (50%) (Hoffman-Laroche) | 1.0 | 1.0 | 0.5 |
| Disodium EDTA (Dissolvine NA-2S, Akzo Nobel) | 0.05 | 0.05 | 0.04 |
| Perfume | 0.25 | 0.3 | 0.2 |
| Water | q.s. | q.s. | q.s. |
| Benefit Phase Compositions |  |  |  |
| Crosslinked acrylic acid-vinyl ester copolymer (Satbylen 30 from 3V) | 1.0 | 1.0 |  |
| Xanthan gum (Keltrol CGT from Kelco) | 1.1 | 1.1 | — |
| Acrylate/Aminoacrylate/C$_{10-30}$ Alkyl PEG-20 Itaconate Copolymer (Structure Plus, National Starch) (20.9%) |  |  | 12.5 |
| Polyquaternium-4 (Celquat H-100, National Starch) |  |  | 1.0 |
| DMDM Hydantoin (Mackstat DM-c, Lonza) (55%) | 0.134 | 0.13 | — |
| Sodium chloride (Morton) | 3.0 | — | — |
| Disodium EDTA (Dissolvine NA-2S, Akzo Nobel) | 0.01 | 0.05 | 0.04 |
| Perfume | 0.1 | 0.2 | 0.15 |
| Triethanolamine (Dow Chemical) | 1.0 | q.s. to pH 6.5 | q.s. to pH 6.5 |
| Tospearl 240 (GE Silicones) | 2.0 | — | — |
| DC9040 Silicone Elastomer Gel[1] (Dow Corning) |  |  | 2.0 |
| 20% Tospearl 240 suspended in Versagel MD500 (Penereco) | — | 5.0 | — |
| D&C Red #30 Talc Lake | 0.05 | — | 0.1 |
| Water | q.s. | q.s. | q.s. |
| Ratio Cleansing Phase/Benefit Phase | 60/40 | 70/30 | 90/10 |

Both the cleansing phase and benefit phase compositions are made according to the general procedure described for examples 1 to 3.

Examples 7-9

|  | Example 7 | Example 8 | Example 9 |
|---|---|---|---|
| Cleansing Phase Composition |  |  |  |
| Sodium Laureth-3 Sulfate (28%) (Procter &Gamble Chemicals) | 14.3 | 14.3 | 14.3 |
| Sodium Lauryl Sulfate (29%) (Procter &Gamble Chemicals) | 34.0 | 30 | 40.9 |
| Cocamidopropyl Betaine (30%) (Goldschmidt Chemical) | 13.3 | 13.3 | 13.3 |
| Coconutmonoethanol amide (Mona Industries) | 2.0 | 2.0 | 2.0 |
| Lauryl Pyrrolidone (Surfadone LP-300, ISP Industries) | 1.0 | 1.0 | 1.0 |
| Alkyl Glycerol Sulfonate | 6 | — | 3.0 |
| Carbopol Aqua SF-1 (Noveon) | — | 1.7 | 1.7 |
| Triethanolamine | — | 0.76 | 0.76 |
| Tospearl 2000 (GE Silicones) | — | — | 2.0 |
| Dimethicone (Viscasil 330M from General Electric) | 4.2 | 6.0 | — |

-continued

|  | Example 7 | Example 8 | Example 9 |
|---|---|---|---|
| Lithium magnesium silicate (Laponite XLS from Southern Clay) | — | — | 1.0 |
| 50% Solution of poly(tert-butyl methacrylate-co-ethylhexyl methacrylate) copolymer in isododecane solvent | 5.0 | 6.0 | — |
| Ethylene Glycol Distearate | 1.5 | — | 1.5 |
| DMDM Hydantoin (Lonza) (55%) | 0.7 | 0.6 | — |
| D&C Red#30 Talc Lake | — | 0.05 | — |
| Citric Acid (50%) (Hoffman-Laroche) | 1.0 | 1.0 | 0.5 |
| Disodium EDTA (Dissolvine NA-2S, Akzo Nobel) | 0.05 | 0.05 | 0.04 |
| Perfume | 0.25 | 0.3 | 0.2 |
| Water | q.s. | q.s. | q.s. |
| Benefit Phase Compositions |  |  |  |
| Carbopol Aqua SF-1 (Noveon) | 5.0 | 5.0 | 10 |
| Cocamidopropyl Betaine (30%) (Goldschmidt Chemical) | 13 | — | 13 |
| Xanthan gum (Keltrol CGT from Kelco) | 1.1 | 1.1 | — |
| Sodium hydroxide | 0.12 | 0.12 | 0.25 |
| Mica (and) Titanium Dioxide (Timiron MP-149, Rona) | 0.2 | 0.2 | 0.2 |
| DMDM Hydantoin (Mackstat DM-c, Lonza) (55%) | 0.134 | 0.13 | — |
| Sodium chloride (Morton) | 3.0 | — | — |
| Disodium EDTA (Dissolvine NA-2S, Akzo Nobel) | 0.01 | 0.05 | 0.04 |
| Perfume | 0.1 | 0.2 | 0.15 |
| Ratio Cleansing Phase/Benefit Phase | 80/20 | 70/30 | 90/10 |

Both the cleansing phase and benefit phase compositions are made according to the general procedure described for examples 1 to 3.

The following compositions may be prepared using conventional formulation and mixing techniques. Where melting or dissolution of solid surfactants or wax components is required these can be added to a premix of the surfactants, or some portion of the surfactants, mixed and heated to melt the solid components, e.g., about 72° C. This mixture can then optionally be processed through a high shear mill and cooled, and then the remaining components are mixed in.

Thickening ingredients should be added according to manufacturer's instructions. Often this involves making a premix in water which is then added to the main mix and, if necessary, adjusted for pH to achieve full thickening performance. Silicone emulsions can be added directly to the compositions, while non-emulsified silicones must first be emulsified to the desired particle size in a premix of surfactant with salt for viscosity control.

Examples 10-16

|  | 10 | 11 | 12 | 13 | 14 | 15 | 16 |
|---|---|---|---|---|---|---|---|
| Cleansing Phase Composition (A) |  |  |  |  |  |  |  |
| Ammonium Laureth-3 Sulfate | 12 | 10 | 6 |  |  |  | 10 |
| Ammonium Lauryl Sulfate | 2 | 6 | 10 |  |  |  | 6 |
| Sodium Laureth-3 Sulfate |  |  |  | 12 | 12 | 12 |  |
| Sodium Lauryl Sulfate |  |  |  | 2 | 2 | 2 |  |
| Cocamidopropyl Betaine | 2 |  |  | 2 | 2 | 2 |  |
| Coconutmonoethanol amide (CMEA, Mona Industries) | 2 | 0.8 | 0.8 | 2 | 2 | 2 | 0.8 |
| Cetyl alcohol | 0 | 0.6 | 0.6 | 0 | 0 | 0 | 0.9 |
| Ethylene Glycol Distearate (EGDS) |  | 1.5 | 1.5 |  |  |  | 1.5 |
| Structure Plus (National Starch) |  | 3 |  |  |  |  |  |
| Carbopol Aqua SF-1 (Noveon) | 3 |  |  | 3 | 3 | 3 |  |
| Crosslinked acrylic acid-vinyl ester copolymer (Satbylen 30 from 3V) |  |  | 1.5 |  |  |  |  |
| Keltrol CGT (Xanthan Gum from Kelco) |  |  | 1 |  |  |  | 2 |
| Guar Hydroxypropyltrimonium Chloride, (N-Hance 3196 from Aqualon) |  |  |  |  |  |  | 0.5 |
| Polyquaterium 10, (UCARE polymer JR-400 from Amerchol) |  |  | 0.5 |  |  |  |  |
| Polyquaterium 10, (UCARE polymer JR-30M from Amerchol) | 0.25 |  |  | 0.25 | 0.25 | 0.25 |  |
| Polymethacrylamidopropyltrimonium Chloride (Polycare 133 from Rhodia) |  | 0.13 |  |  |  |  |  |

-continued

|  | 10 | 11 | 12 | 13 | 14 | 15 | 16 |
|---|---|---|---|---|---|---|---|
| Dimethicone (Viscasil 330M from General Electric) |  | 2 | 3 |  |  |  | 2.4 |
| Dow Corning 1664 (silicone microemulsion) |  |  |  | 2 |  |  |  |
| Dow Corning 1870 (silicone nanoemulsion) | 2 |  |  |  | 2 | 2 |  |
| Puresyn 6 (1-decene homopolymer) |  | 0.3 | 0.6 |  |  |  |  |
| Zinc Pyrithione |  |  |  |  |  |  | 1 |
| Kathon CG (Rhom & Haas) | 0.0005 | 0.0005 | 0.0005 | 0.0005 | 0.0005 | 0.0005 | 0.0008 |
| Benzyl Alcohol |  |  |  |  |  |  | 0.0225 |
| Disodium EDTA (Dissolvine NA-2S, Akzo Nobel) | 0.1274 | 0.1274 | 0.1274 | 0.1274 | 0.1274 | 0.1274 |  |
| Sodium chloride (Morton) | 0.5 | 0.7 | 0.8 | 0.5 | 0.5 | 0.5 | 0.7 |
| Sodium Citrate Dihydrate | 0.4 | 0.4 | 0.4 | 0.4 | 0.4 | 0.4 | 0.4 |
| Citric Acid (Hoffman-Laroche) | 0.15 | 0.15 | 0.08 | 0.15 | 0.15 | 0.15 | 0.12 |
| Perfume | 0.6 | 0.6 | 0.6 | 0.6 | 0.6 | 0.6 | 0.6 |
| Water | q.s. | q.s. | q.s. | q.s. | q.s. | q.s. | q.s. |
| Benefit Phase Compositions (B) |  |  |  |  |  |  |  |
| Ammonium Laureth-3 Sulfate | 12 | 10 | 6 |  |  |  | 10 |
| Ammonium Lauryl Sulfate | 2 | 6 | 10 |  |  |  | 6 |
| Sodium Laureth Sulfate |  |  |  |  | 14 | 5 |  |
| Sodium Trideceth Sulfate |  |  |  | 14.6 |  |  |  |
| Sodium Lauroamphoacetate |  |  |  |  | 7 | 18 |  |
| Cocamidopropyl Betaine (30%) (Goldschmidt Chemical) | 2 |  |  |  |  |  |  |
| Lauric acid |  |  |  |  | 3 | 1.6 |  |
| Coconutmonoethanol amide (Mona Industries) | 2 | 0.8 | 0.8 | 3 |  |  | 0.8 |
| Ethylene Glycol Distearate (EGDS) |  | 1.5 | 1.5 |  |  |  | 1.5 |
| Cetyl Alcohol |  | 0.6 | 0.6 |  |  |  | 0.9 |
| Structure Plus (National Starch) |  | 3 |  |  |  |  |  |
| Carbopol Aqua SF-1 (30%) (Noveon) | 3 |  |  | 3 | 3 | 3 |  |
| Crosslinked acrylic acid-vinyl ester copolymer (Satbylen 30 from 3V) |  |  | 1.5 |  |  |  |  |
| Xanthan gum (Keltrol CGT from Kelco) |  |  | 1 |  |  |  | 2 |
| Trihydroxystearin |  |  |  |  |  | 0.5 |  |
| Polyquaterium 10, (UCARE polymer JR-400 from Amerchol) |  |  | 0.5 |  |  |  |  |
| Polyquaterium 10, (UCARE polymer JR-30M from Amerchol) | 0.25 |  |  |  | 0.5 |  |  |
| Polymethacrylamidopropyltrimonium Chloride (Polycare 133 from Rhodia) |  | 0.13 |  | 0.13 |  |  |  |
| Dimethicone (Viscasil 330M from General Electric) |  | 2 | 3 |  |  | 2.3 | 1.0 |
| Dow Corning 1664 (silicone microemulsion) | 2 |  |  | 2 | 3 |  |  |
| Puresyn 6 (1-decene homopolymer) |  | 0.3 | 0.6 |  |  |  |  |
| Zinc Pyrithione |  |  |  |  | 2 |  | 1 |
| Kathon CG (Rhom & Haas) | 0.0005 | 0.0005 | 0.0005 | 0.0005 | 0.0008 | 0.0005 | 0.0008 |
| Benzyl Alcohol |  |  |  |  | 0.0225 |  | 0.0225 |
| Disodium EDTA (Dissolvine NA-2S, Akzo Nobel) | 0.1274 | 0.1274 | 0.1274 | 0.1274 |  | 0.1274 |  |

|  | 10 | 11 | 12 | 13 | 14 | 15 | 16 |
|---|---|---|---|---|---|---|---|
| Sodium chloride (Morton) |  |  |  | 3 |  |  |  |
| Sodium Citrate Dihydrate | 0.4 | 0.4 | 0.4 | 0.4 | 0.4 | 0.4 | 0.4 |
| Citric Acid (Hoffman-Laroche) | 0.15 | 0.15 | 0.08 | 0.15 | 0.15 | 0.15 | 0.12 |
| FD&C Blue # 1 Aluminum Lake (Sun Chem.) | .003 | .002 |  |  |  |  |  |
| D&C Red # 7 Ca Lake (Sun Chem.) |  | .01 | .01 |  |  |  |  |
| D&C Red # 30 Talc Lake (Sun Chem.) |  |  |  | .002 | .02 | .02 | .04 |
| Perfume | 0.6 | 0.6 | 0.8 | 0.6 | 0.6 | 0.6 | 1 |
| Water | qs | qs | qs | qs | qs | qs | qs |
| Ratio Cleansing Phase/Benefit Phase | 90/10 | 70/30 | 50/50 | 50/50 | 60/40 | 70/30 | 50/50 |

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

All documents cited in the Background, Summary of the Invention, and Detailed Description of the Invention are, in relevant part, incorporated herein by reference; the citation of any document is not to be construed as an admission that it is prior art with respect to the present invention.

What is claimed is:

1. A multi-phase personal care composition comprising:
   a) at least one visibly clear cleansing phase comprising:
      at least one surfactant selected from the group consisting of alkyl and alkyl ether sulfates; and
      at least one thickener, wherein said thickener is selected from polymeric thickeners; and
   b) at least one opaque aqueous benefit phase comprising:
      a thickener mixture of a fatty acid and trihydroxystearin; and at least one benefit agent selected from the group consisting of styling polymers, silicones, crosslinked silicone elastomers, peralkylene hydrocarbons, and hair coloring agents or dyes;
   wherein said at least one cleansing phase and said at least one benefit phase are visually distinct phases that are packaged in physical contact with one another; and
   wherein said cleansing phase and said benefit phase form a visible pattern or arrangement that is unchanged for a period of at least about 180 days, when said cleansing phase and said benefit phase sit undisturbed in physical contact with one another at ambient conditions.

2. The multi-phase personal care composition of claim 1 wherein said surfactant is selected from the group consisting of anionic surfactants, nonionic surfactants, zwitterionic surfactants, amphoteric surfactants, soap, and mixtures thereof.

3. The multi-phase personal care composition of claim 1 wherein aid at least one aqueous benefit phase further comprises at least one benefit agent selected from the group consisting of anti-dandruff actives, humectants, water soluble nonionic polymers, cationic polymers, conditioning agents, and particles.

4. The multi-phase personal care composition of claim 1 wherein aid at least one aqueous benefit phase further comprises at least one surfactant.

5. The multi-phase personal care composition of claim 1 wherein aid at least one cleaning phase and aid at least one aqueous benefit phase are visually distinct phases due to inclusion of a colorant in aid at least one cleansing phase, in aid at least one aqueous benefit phase, and/or in both of aid at least one cleansing phase and aid at least one aqueous benefit phase.

6. The multi-phase personal care composition of claim 1 wherein aid visually distinct phases form a pattern selected from group consisting of striped, geometric, marbled, and combinations thereof.

7. The multi-phase personal care composition of claim 1 wherein the density difference between said at least one cleansing phase and said at least one aqueous benefit phase is less than about 0.30 g/cm3.

8. The multi-phase personal care composition of claim 1 wherein the viscosity of said at least one cleansing phase and said at least one aqueous benefit phase arc in the range of from about 10,000 to about 200,000,000 centipoise at stress measurements of from about 1 to about 20 pascals at about 25° C.

9. The multi-phase personal care composition of claim 1 wherein the viscosity of said at least one cleansing phase and said at least one aqueous benefit phase are in the range of from about 100,000 to about 100,000,000 centipoise at stress measurements of from about 1 to about 20 pascals at about 25° C.

10. The multi-phase personal care composition of claim 1 wherein said surfactant in the cleaning phase further comprises Lauryl Pyrrolidone surfactant.

11. The multi-phase personal care composition of claim 1 further comprising a water-soluble dye in said at least one cleansing phase and/or said at least one aqueous benefit phase.

12. The multi-phase personal care composition of claim 11 further comprising a non-soluble dye in said at least one aqueous benefit phase.

13. The multi-phase personal care composition of claim 1 further comprising a non-soluble dye in said at least one aqueous benefit phase.

14. A method of delivering conditioning benefits to hair or skin, said method comprising the steps of:
   a) topically applying an effective amount of a composition according to claim 1 onto said hair or skin; and
   b) optionally rinsing said hair or skin with water.

15. A method of delivering hair styling benefits to hair, aid method comprising the steps of:
  a) topically applying an effective amount of a composition according to claim 1 onto hair; and
  b) rinsing aid hair or skin with water.

16. A method of delivering hair coloring benefits to hair, aid method comprising the steps of:
  a) topically applying an effective amount of a composition according to claim 1 onto said hair; and
  b) rinsing aid hair or skin with water.

17. A method of delivering anti-dandruff benefits, aid method comprising the steps of:
  a) topically applying an effective amount of a composition according to claim 3 onto hair or skin; and
  b) rinsing aid hair or skin with water.

18. A method of delivering volumizing benefits to hair, aid method comprising the steps of:
  a) topically applying an effective amount of a composition according to claim 3 onto aid hair; and
  b) optionally rinsing aid hair with water.

* * * * *